United States Patent
Aissaoui et al.

(10) Patent No.: US 7,067,519 B2
(45) Date of Patent: Jun. 27, 2006

(54) 7,8,9,10-TETRAHYDRO-6H-AZEPINO, 6,7,8,9-TETRAHYDRO-PYRIDO AND 2,3-DIHYDRO-2H-PYRROLO[2,1-B]-QUINAZOLINONE DERIVATIVES

(76) Inventors: Hamed Aissaoui, 04, Alle des Griottes, F-68840 Pulversheim (FR); Martine Clozel, Winterhalde 3b, CH-4102 Binningen (CH); Walter Fischli, Obertorweg 64, CH-4123 Allschwil (CH); Ralf Koberstein, Bergstrasse 34 b, D-79539 Lörrach (DE); Thierry Sifferlen, 6, rue de Thann, F-68116 Guewenheim (FR); Thomas Weller, Hoelzlistrasse 58, CH-4102 Binningen (CH)

( * ) Notice: Subject to any disclaimer, the term of this patent is extended or adjusted under 35 U.S.C. 154(b) by 0 days.

(21) Appl. No.: 10/489,350

(22) PCT Filed: Jul. 8, 2003

(86) PCT No.: PCT/EP03/07297

§ 371 (c)(1),
(2), (4) Date: Aug. 16, 2004

(87) PCT Pub. No.: WO2004/004733

PCT Pub. Date: Jan. 15, 2004

(65) Prior Publication Data

US 2005/0009852 A1    Jan. 13, 2005

(30) Foreign Application Priority Data

Jul. 9, 2002  (WO)  ..................... PCT/EP02/07608

(51) Int. Cl.
*A61K 31/517*   (2006.01)
*A61K 31/536*   (2006.01)
*C07D 487/04*   (2006.01)
*C07D 498/04*   (2006.01)
*C07D 513/04*   (2006.01)

(52) U.S. Cl. ..................... 514/257; 514/267; 540/580; 544/252

(58) Field of Classification Search ................ 514/257, 514/267; 540/580; 544/252
See application file for complete search history.

(56) References Cited

U.S. PATENT DOCUMENTS

| 4,460,771 A | * | 7/1984 | Meszaros et al. ............ 544/282 |
| 4,472,398 A | * | 9/1984 | Meszaros et al. ........ 514/259.4 |
| 4,588,526 A | * | 5/1986 | Hermecz et al. ............ 540/586 |
| 4,678,499 A | * | 7/1987 | Pasteris et al. ............. 504/214 |
| 5,753,664 A | * | 5/1998 | Aono et al. .............. 514/259.4 |
| 6,057,315 A | * | 5/2000 | Domagala et al. ........ 514/224.5 |
| 6,676,976 B1 | * | 1/2004 | Chattopadhyay et al. ... 424/725 |
| 6,825,184 B1 | * | 11/2004 | Cirillo et al. ................ 514/183 |
| 2003/0225111 A1 | * | 12/2003 | Hennequin et al. .... 514/260.01 |
| 2004/0266798 A1 | * | 12/2004 | Bavetsias ..................... 514/267 |

FOREIGN PATENT DOCUMENTS

| WO | WO-99/09024 A1 | 2/1999 |
| WO | WO-99/58533 A1 | 11/1999 |
| WO | WO-00/47576 A1 | 8/2000 |
| WO | WO-00/47577 A1 | 8/2000 |
| WO | WO-00/47580 A1 | 8/2000 |
| WO | WO-01/85693 A1 | 11/2001 |
| WO | WO-01/96302 A1 | 12/2001 |
| WO | WO-02/44172 A1 | 6/2002 |

OTHER PUBLICATIONS

Kamal, A. et. al., "Chemoenzymatic Synthesis of Pyrrolo[2,1-b]quinazolinones: . . . ", J. Org. Chem., 2001, vol. 66, pp. 997-1001.*
Neal, Bramson H. ,"Oxindole-Based Inhibitors of Cyclin-Dependent Kinase 2 (CDK2): Deisign, Synthesis, Enxymatic Activities, and X-ray Crystallographic Analysis", J.Med.Chem 2001, 44, pp. 4339-4358.
Bhardwaj, V., et al, "A Synthesis of 11H-Pyrido [2,1-b] Quinazolin-11-Ones," Indian Journal of Heterocyclic Chemistry 1999, 9, pp. 173-176.
Karinov, A., "Synthesis of Methoxy-and Hydroxy-Substituted Deoxyvasicinones and Deoxypecanines," Chemistry of Natural Compounds, 1982, 18, 4, pp. 466-472.
Giencke, A., "Desmethyl(trifluomethyl)actinomycine," Liebigs Ann.Chem., 1990, pp. 569-179.
Chemelli R.M. et al., "Narcolepsy in orexin Knockout Mice: Molecular Genetics of Sleep Regulation," Cell, 1999, 98, pp. 437-451.

(Continued)

*Primary Examiner*—James O. Wilson
*Assistant Examiner*—Tamthom N. Truong
(74) *Attorney, Agent, or Firm*—Dickstein, Shapiro, Morin & Oshinsky, LLP.

(57) ABSTRACT

The invention relates to novel 7,8,9,10-tetrahydro-6H-azepino, 6,7,8,9-tetrahydro-pyrido and 2,3-dihydro-2H-pyrrolo [2,1-b]-quinazolinone derivatives and their use as active ingredients in the preparation of pharmaceutical compositions. The invention also concerns related aspects including processes for the preparation of the compounds, pharmaceutical compositions containing one or more of those compounds and especially their use as orexin receptor antagonists.

8 Claims, No Drawings

OTHER PUBLICATIONS

Sakurai T., et al., "Orexins and Orexin Receptors: A Family of Hypothalamic Neuropeptides and G Protein-Coupled Receptors that Regulate Feeding Behavior," Cell, 1998, 92, pp. 573-585.

Kamal, A. et al., "Chemoenzymatic Synthesis of Pyrrolo[2,1-b]quinazolinones: Lipase-Catalyzed Resolution of Vasicinone," J. Org. Chem, 2001, 66, pp. 997-1001.

March J., "Aliphatic Nucleophilic Substitution," Advanced Organic Chemistry-Reactions, Mechanisms and Structure, 1992, p. 418, 4th edition.

Follope, M.P., et al. "Synthese et etude de l'activite cytotoxique in vitro et antitumorale in vivo de nouvelles pyrrolo[2,1-c][1,4] benxodiazepines: partie I," Eur. J.Med. Chem., 1992, 27, pp. 291-295.

Deady L.W., et al., "Synthesis and Antitumor Properties of N-[2-(Dimethylamino)ethyl]carboxamide Derivatives of Fused Tetracyclic Quinolines and Quinoxalines: A New Class of Putative Topoisomerase Inhibitors," J.Med.Chem., 1997, 40, pp. 2040-2046.

Hughes, P., et al., "Synthetic Entries to 6-Fluoro-7-substituted Indole Derivatives," J.Heterocyclic Chem, 1990, 27, pp. 2151-2163.

Rowley, M. et al., "3-Acyl-4-hydroxyquinolin-2(1H)-ones. Systematically Active Anticonvulsants Acting by Antagonism at the Glycine Site of the N-Methyl-D-Aspartate Receptor Complex," J.Med.Chem., 1993, 36, pp. 3386-3396.

* cited by examiner

7,8,9,10-TETRAHYDRO-6H-AZEPINO, 6,7,8,9-TETRAHYDRO-PYRIDO AND 2,3-DIHYDRO-2H-PYRROLO[2,1-B]-QUINAZOLINONE DERIVATIVES

The present invention relates to novel 7,8,9,10-tetrahydro-6H-azepino, 6,7,8,9-tetrahydro-pyrido and 2,3-dihydro-2H-pyrrolo[2,1-b]-quinazolinone derivatives of the general formula I and their use as pharmaceuticals. The invention also concerns related aspects including processes for the preparation of the compounds, pharmaceutical compositions containing one or more compounds of formula I, and especially their use as orexin receptor antagonists.

The orexins (hypocretins) comprise two neuropeptides produced in the hypothalamus: the orexin A (OX-A) (a 33 aminoacid peptide) and the orexin B (OX-B) (a 28 aminoacid peptide) (Sakurai T. et al., Cell, 1998, 92, 573–585). Orexins are found to stimulate food consumption in rats suggesting a physiological role for these peptides as mediators in the central feedback mechanism that regulates feeding behavior (Sakurai T. et al., Cell, 1998, 92, 573–585). On the other hand, it was also proposed that orexins regulate states of sleep and wakefulness opening potentially novel therapeutic approaches for narcoleptic patients (Chemelli R. M. et al., Cell, 1999, 98, 437–451). Two orexin receptors have been cloned and characterized in mammals. They belong to the superfamily of G-protein coupled receptor (Sakurai T. et al., Cell, 1998, 92, 573–585): the orexin-1 receptor ($OX_1$) is selective for OX-A and the orexin-2 receptor ($OX_2$) is capable to bind OX-A as well as OX-B.

Orexin receptors are found in the mammalian host and may be responsible for many biological functions such as pathologies including, but not limited to, depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delerium; dementia; severe mental retardation and dyskinesias such as Huntington's disease and Tourette syndrome; feeding disorders such as anorexia, bulimia, cachexia and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; inflammatory bowel disease; gastric diskinesia; gastric ulcus; Froehlich's syndrome; adrenohypophysis disease; hypophysis disease; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischaemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegerative disorders including nosological entities such as disinhibition-dementia-parkinsonism-amyotrophy complex; pallido-ponto-nigral degeneration epilepsy; seizure disorders and other diseases related to orexin.

The present invention provides 7,8,9,10-tetrahydro-6H-azepino, 6,7,8,9-tetrahydro-pyrido and 2,3-dihydro-2H-pyrrolo[2,1-b]-quinazolinone derivatives which are non-peptide antagonists of human orexin receptors. In particular, these compounds are of potential use in the treatment of obesity and/or sleep disorders.

International Patent Applications WO099/09024, WO099/58533, WO00/47577, WO00/47580, disclose phenyl urea derivatives and WO00/47576, discloses quinolinyl cinnamide derivatives as orexin antagonists.

Furthermore, WO 0196302 has been published wherein piperidine derivatives as $OX_1$ and $OX_2$ antagonists are disclosed and WO 0185693 has been published wherein N-acyltetrahydroisoquinoline derivatives as selective $OX_2$ antagonists are disclosed. In addition, WO 0244172 describes morpholine derivatives as antagonists of orexin receptors.

The novel compounds of the present invention belong to an entirely different class of low molecular weight compounds as compared to all prior art orexin receptor antagonists so far published.

The present invention relates to novel 7,8,9,10-tetrahydro-6H-azepino, 6,7,8,9-tetrahydro-pyrido and 2,3-dihydro-2H-pyrrolo[2,1-b]-quinazolinone derivatives of the general formula (I).

Formula (I)

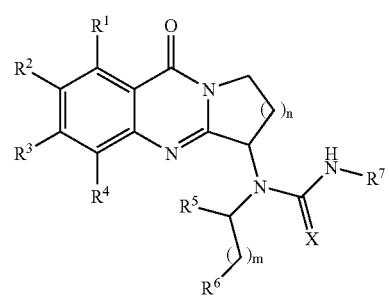

wherein:

X is O or S;

n is the integer 1, 2, or 3;

m is the integer 0, 1, 2, 3;

$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclyl-lower alkyloxy, $R^8CO—$, $NR^9R^{10}CO—$, $R^9R^{10}N—$, $R^8OOC—$, $R^8SO_2NH—$, $R^{11}—CO—NH$ or $R^2$ and $R^3$ together or $R^1$ and $R^2$ together or $R^3$ and $R^4$ together may form with the phenyl ring a five, six or seven-membered ring containing one or two oxygen atoms which are separated by at least one carbon atom;

$R^5$ represents aryl, aralkyl, lower alkyl, cycloalkyl, cycloalkyl-lower alkyl, heterocyclyl or heterocyclyl-lower alkyl;

$R^6$ represents hydrogen, lower alkyl, trifluoromethyl, —$(CH_2)_m$—OH, —$(CH_2)_m$—O-lower alkyl, —$(CH_2)_m$—$CO_2H$, —$(CH_2)_m$—$CO_2$-lower alkyl, —$(CH_2)_m CONH_2$, or —$(CH_2)_m$—CONH-lower alkyl, or —$(CH_2)_m$—CON-(lower alkyl)$_2$, or —$(CH_2)_m$—N-(lower alkyl)$_2$;

$R^7$ represents aryl, aralkyl, lower alkyl, lower alkenyl, cycloalkyl, cycloalkyl-lower alkyl, heterocyclyl or heterocyclyl-lower alkyl;

$R^8$ represents lower alkyl, aryl, aralkyl, heterocyclyl or heterocyclyl-lower alkyl;

$R^9$ and $R^{10}$ independently represent hydrogen, alkyl, cycloalkyl, cycloalkyl-lower alkyl, aryl, aralkyl, heterocyclyl or heterocyclyl-lower alkyl;

$R^{11}$ represents alkyl, aryl, cycloalkyl, heterocyclyl, $R^9R^{10}N$— or $R^8O$—.

The compounds of formula I can contain one or more asymmetric centres and can be present in the form of optically pure enantiomers, mixtures of enantiomers such as, for example, racemates, optically pure diastereoisomers, mixtures of diastereoisomers, diastereoisomeric racemates, mixture of diastereoisomeric racemates, or meso forms and pharmaceutically acceptable salts thereof.

In the present description the term "lower alkyl", alone or in combination, signifies a straight-chain or branched-chain alkyl group with 1 to 8 carbon atoms, preferably a straight or branched-chain alkyl group with 1–5 carbon atoms. Examples of straight-chain and branched $C_1$–$C_8$ alkyl groups are methyl, ethyl, n-propyl, isopropyl, n-butyl, n-pentyl, n-hexyl, n-heptyl, n-octyl, isobutyl, tert-butyl, the isomeric pentyls, the isomeric hexyls, the isomeric heptyls and the isomeric octyls, preferably methyl, ethyl, n-proplyl, isopropyl, n-butyl, 2-butyl, tert-butyl and n-pentyl.

The term "lower alkenyl", alone or in combination, signifies a straight-chain or branched-chain alkenyl group with 2 to 5 carbon atoms, preferably allyl and vinyl.

The term "lower alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

Lower alkenyloxy groups are preferably vinyloxy and allyloxy.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, cyclobutyl, cyclopentyl, cyclohexyl, cycloheptyl and cyclooctyl, preferably cyclopropyl, cyclohexyl or lower alkyl substituted cycloalkyl which may preferably be substituted with lower alkyl such as methyl-cyclopropyl, dimethyl-cyclopropyl, methyl-cyclobutyl, methyl-cyclopentyl, methyl-cyclohexyl, dimethyl-cyclohexyl, The term "aryl", alone or in combination, signifies a phenyl or naphthyl group which optionally carries one or more substituents, preferably one or two substituents, each independently selected from cyano, halogen, hydroxy, lower alkyl, lower alkenyl, lower alkoxy, lower alkenyloxy, nitro, trifluoromethyl, trifluoromethoxy, amino, carboxy, alkoxy-carbonyl and the like, such as phenyl, p-tolyl, 4-methoxyphenyl, 4-tert-butoxyphenyl, 4-fluorophenyl, 2-chlorophenyl, 4-hydroxyphenyl, 1-naphthyl and 2-naphthyl. Preferred are carboxyphenyl, lower alkoxy-phenyl, hydroxyphenyl and particularly phenyl.

The term "aralkyl", alone or in combination, signifies an alkyl or cycloalkyl group as previously defined in which one hydrogen atom has been replaced by an aryl group as previously defined. Preferred are benzyl and benzyl substituted in the phenyl ring with hydroxy, lower alkyl, lower alkoxy or halogen preferably fluorine. Particularly preferred is benzyl.

For the term "heterocyclyl" and "heterocyclyl-lower alkyl", the heterocyclyl group is preferably a 5- to 10-membered monocyclic or bicyclic ring, which may be saturated, partially unsaturated or aromatic containing for example 1, 2 or 3 heteroatoms selected from oxygen, nitrogen and sulphur which may be the same or different. Example of such heterocyclyl groups are pyrrolidinyl, piperidinyl, piperazinyl, morpholinyl, pyridyl, pyrimidinyl, pyrazinyl, pyridazinyl, quinolyl, isoquinolyl, thienyl, thiazolyl, isothiazolyl, furyl, imidazolyl, pyrazolyl, pyrrolyl, indazolyl, indolyl, isoindolyl, isoxazolyl, oxazolyl, quinoxalinyl, phthalazinyl, cinnolinyl, dihydropyrrolyl, pyrrolidinyl, isobenzofuranyl, tetrahydrofuranyl, dihydropyranyl. The heterocyclyl group may have up to 5, preferably 1, 2 or 3 optional substituents. Examples of suitable substituents include halogen, lower alkyl, amino, nitro, cyano, hydroxy, lower alkoxy, carboxy and lower alkyloxy-carbonyls.

The term "halogen" signifies fluorine, chlorine, bromine or iodine and preferably chlorine and fluorine and particularly fluorine.

The term "carboxy", alone or in combination, signifies a —COOH group. Preferred compounds are compounds of the general formula I wherein n is the integer 1 or 2, m is the integer 0, 1 or 2, $R^1$, $R^2$, $R^3$, $R^4$, $R^5$, $R^6$ and $R^7$ have the meaning given in the formula I above and X represents oxygen.

Examples of preferred compounds are:

1-(9-Oxo-1,2,3,9-tetrahydro-pyrrolo[2,1-b]quinazolin-3-yl)-1-(1-phenyl-ethyl)-3-(2-n-propyl-phenyl)-urea;

3-Biphenyl-2-yl-(9-oxo-1,2,3,9-tetrahydro-pyrrolo[2,1-b]quinazolin-3-yl)-1-(1-phenyl-ethyl)-urea;

3-Naphthalen-1-yl-1-(9-oxo-1,2,3,9-tetrahydro-pyrrolo[2,1-b]quinazolin-3-yl)-1-(1-phenyl-ethyl)-urea;

3-(2-Ethyl-phenyl)-1-(9-oxo-1,2,3,9-tetrahydro-pyrrolo[2,1-b]quinazolin-3-yl)-1-(1-phenyl-ethyl)-urea;

3-(2-Ethoxy-phenyl)-1-(9-oxo-1,2,3,9-tetrahydro-pyrrolo[2,1-b]quinazolin-3-yl)-1-(1-phenyl-ethyl)-urea;

3-(2-Ethyl-phenyl)-1-(6-fluoro-9-oxo-1,2,3,9-tetrahydro-pyrrolo[2,1-b]quinazolin-3-yl)-1-(1-phenyl-ethyl)-urea;

3-Biphenyl-2-yl-1-(6-fluoro-9-oxo-1,2,3,9-tetrahydro-pyrrolo[2,1-b]quinazolin-3-yl)-1-(1-phenyl-ethyl)-urea;

1-(6-Fluoro-9-oxo-1,2,3,9-tetrahydro-pyrrolo[2,1-b]quinazolin-3-yl)-1-(1-phenyl-ethyl-3-(2-n-propyl-phenyl)-urea;

1-(6-Fluoro-9-oxo-1,2,3,9-tetrahydro-pyrrolo[2,1-b]quinazolin-3-yl)-1-(1-phenyl-ethyl)-3-(2-trifluoromethoxy-phenyl)-urea;

1-(6-Fluoro-9-oxo-1,2,3,9-tetrahydro-pyrrolo[2,1-b]quinazolin-3-yl)-3-(2-isopropyl-phenyl)-1-(1-phenyl-ethyl)-urea;

1-(6-Fluoro-9-oxo-1,2,3,9-tetrahydro-pyrrolo[2,1-b]quinazolin-3-yl)-3-naphthalen-1-yl-1(1-phenyl-ethyl)-urea;

1-(7-Fluoro-9-oxo-1,2,3,9-tetrahydro-pyrrolo[2,1-b]quinazolin-3-yl)-1-(phenyl-ethyl)-3-(2-n-propyl-phenyl)-urea;

1-(7-Fluoro-9-oxo-1,2,3,9-tetrahydro-pyrrolo[2,1-b]quinazolin-3-yl)-1-(phenyl-ethyl)-3-(2-trifluoromethoxy-phenyl)-urea;
3-Biphenyl-2-yl-1-(7-fluoro-9-oxo-1,2,3,9-tetrahydro-pyrrolo[2,1-b]quinazolin-3-yl)-1-(1-phenyl-ethyl)-urea;
3-(2-Ethyl-phenyl)-1-(7-fluoro-9-oxo-1,2,3,9-tetrahydro-pyrrolo[2,1-b]quinazolin-3-yl)-1-(1-phenyl-ethyl)-urea;
1-(6-Chloro-9-oxo-1,2,3,9-tetrahydro-pyrrolo[2,1-b]quinazolin-3-yl)-1-(phenyl-ethyl)-3-(2-n-propyl-phenyl)-urea;
1-(7-Chloro-9-oxo-1,2,3,9-tetrahydro-pyrrolo[2,1-b]quinazolin-3-yl)-3-(2-ethyl-phenyl)-1-(1-phenyl-ethyl)-urea;
1-(7-Chloro-9-oxo-1,2,3,9-tetrahydro-pyrrolo[2,1-b]quinazolin-3-yl)-3-naphthalen-1-yl-1(1-phenyl-ethyl)-urea;
1-(7-Chloro-9-oxo-1,2,3,9-tetrahydro-pyrrolo[2,1-b]quinazolin-3-yl)-3-(2-isopropyl-phenyl)-1-(1-phenyl-ethyl)-urea;
1-(7-Chloro-9-oxo-1,2,3,9-tetrahydro-pyrrolo[2,1-b]quinazolin-3-yl)-1-(1-phenyl-ethyl)-3-(2-n-propyl-phenyl)-urea;
1-(7-Chloro-9-oxo-1,2,3,9-tetrahydro-pyrrolo[2,1-b]quinazolin-3-yl)-1-(phenyl-ethyl)-3-(2-trifluoromethoxy-phenyl)-urea;
3-Biphenyl-2-yl-1-(7-chloro-9-oxo-1,2,3,9-tetrahydro-pyrrolo[2,1-b]quinazolin-3-yl)-1-(1-phenyl-ethyl)-urea;
1-(8-Chloro-9-oxo-1,2,3,9-tetrahydro-pyrrolo[2,1-b]quinazolin-3-yl)-1-(1-phenyl-ethyl)-3-(2-n-propyl-phenyl)-urea;
1-(8-Chloro-9-oxo-1,2,3,9-tetrahydro-pyrrolo[2,1-b]quinazolin-3-yl)-3-(2-ethyl-phenyl)-1-(1-phenyl-ethyl)-urea;
1-(8-Chloro-9-oxo-1,2,3,9-tetrahydro-pyrrolo[2,1-b]quinazolin-3-yl)-1-(1-phenyl-ethyl)-3-(2-trifluoromethoxy-phenyl)-urea;
1-(8-Chloro-9-oxo-1,2,3,9-tetrahydro-pyrrolo[2,1-b]quinazolin-3-yl)-3-naphthalen-1-yl-1-(1-phenyl-ethyl)-urea;
3-Biphenyl-2-yl-1-(8-chloro-9-oxo-1,2,3,9-tetrahydro-pyrrolo[2,1-b]quinazolin-3-yl)-1-(1-phenyl-ethyl)-urea;
1-(8-Chloro-9-oxo-1,2,3,9-tetrahydro-pyrrolo[2,1-b]quinazolin-3-yl)-3-(2-isopropyl-phenyl)-1-(1-phenyl-ethyl)-urea;
3-Biphenyl-2-yl-1-(6,7-difluoro-9-oxo-1,2,3,9-tetrahydro-pyrrolo[2,1-b]quinazolin-3-yl)-1-(1-phenyl-ethyl)-urea;
1-(6,7-Difluoro-9-oxo-1,2,3,9-tetrahydro-pyrrolo[2,1-b]quinazolin-3-yl)-1-(phenyl-ethyl)-3-(2-trifluoromethoxy-phenyl)-urea;
1-(6,7-Difluoro-9-oxo-1,2,3,9-tetrahydro-pyrrolo[2,1-b]quinazolin-3-yl)-1-(1-phenyl-ethyl)-3-(2-n-propyl-phenyl)-urea;
1-(6,7-Difluoro-9-oxo-1,2,3,9-tetrahydro-pyrrolo[2,1-b]quinazolin-3-yl)-3-(2-ethyl-phenyl)-1-(1-phenyl-ethyl)-urea;
3-Biphenyl-2-yl-1-butyl-1-(9-oxo-1,2,3,9-tetrahydro-pyrrolo[2,1-b]quinazolin-3-yl)-urea;
1-Butyl-1-(9-oxo-1,2,3,9-tetrahydro-pyrrolo[2,1-b]quinazolin-3-yl)-3-(2-n-propyl-phenyl)-urea;
1-Benzyl-3-biphenyl-2-yl-1-(9-oxo-1,2,3,9-tetrahydro-pyrrolo[2,1-b]quinazolin-3-yl)-urea;
1-Benzyl-3-(2-ethoxy-phenyl)-1-(9-oxo-1,2,3,9-tetrahydro-pyrrolo[2,1-b]quinazolin-3-yl)-urea;
1-Benzyl-1-(9-oxo-1,2,3,9-tetrahydro-pyrrolo[2,1-b]quinazolin-3-yl)-3-(2-n-propyl-phenyl)-urea;
3-Biphenyl-2-yl-1-(11-oxo-6,8,9,11-tetrahydro-7H-pyrido[2,1-b]quinazolin-6-yl)-1-(1-phenyl-ethyl)-urea;
1-(11-oxo-6,8,9,11-tetrahydro-7H-pyrido[2,1-b]quinazolin-6-yl)-1-(1-phenyl-ethyl)-3-(2-n-propyl-phenyl)-urea;
3-(2-Ethyl-phenyl)-1-(11-oxo-6,8,9,11-tetrahydro-7H-pyrido[2,1-b]quinazolin-6-yl)-1-(1-phenyl-ethyl)-urea;
3-(2-Ethoxy-phenyl)-1-(11-oxo-6,8,9,11-tetrahydro-7H-pyrido[2,1-b]quinazolin-6-yl)-1-(1-phenyl-ethyl)-urea;
3-Naphthalen-1-yl-1-(11-oxo-6,8,9,11-tetrahydro-7H-pyrido[2,1-b]quinazolin-6-yl)-1-(1-phenyl-ethyl)-urea;
3-Biphenyl-2-yl-1-(2,3-difluoro-11-oxo-6,8,9,11-tetrahydro-7H-pyrido[2,1-b]quinazolin-6-yl)-1-(1-phenyl-ethyl)-urea;
1-(2,3-Difluoro-11-oxo-6,8,9,11-tetrahydro-7H-pyrido[2,1-b]quinazolin-6-yl)-1-(1-phenyl-ethyl)-3-(2-n-propyl-phenyl)-urea;
1-(2,3-Difluoro-11-oxo-6,8,9,11-tetrahydro-7H-pyrido[2,1-b]quinazolin-6-yl)-3-(2-ethyl-phenyl)-1-(1-phenyl-ethyl)-urea;
1-(2,3-Difluoro-11-oxo-6,8,9,11-tetrahydro-7H-pyrido[2,1-b]quinazolin-6-yl)-3-(2-ethoxy-phenyl)-1-(1-phenyl-ethyl)-urea;
3-Biphenyl-2-yl-1-(3-fluoro-11-oxo-6,8,9,11-tetrahydro-7H-pyrido[2,1-b]quinazolin-6-yl)-1-(1-phenyl-ethyl)-urea;
1-(3-Fluoro-11-oxo-6,8,9,11-tetrahydro-7H-pyrido[2,1-b]quinazolin-6-yl)-1-(1-phenyl-ethyl)-3-(2-n-propyl-phenyl)-urea;
3-(2-Ethoxy-phenyl)-1-(3-fluoro-11-oxo-6,8,9,11-tetrahydro-7H-pyrido[2,1-b]quinazolin-6-yl)-1-(1-phenyl-ethyl)-urea;
3-(2-Ethyl-phenyl)-1-(3-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-1-(1-phenyl-ethyl)-3-(2-n-propyl-phenyl)-urea;
3-(2-Ethyl-phenyl)-1-(2-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-1-(1-phenyl-ethyl)-3-(2-trifluoromethoxy-phenyl)-urea;
3-(2-Ethoxy-phenyl)-1-(2-fluoro-11-oxo-6,8,9,11-tetrahydro-7H-pyrido[2,1-b]quinazolin-6-yl)-1-(1-phenyl-ethyl)-urea;
3-Biphenyl-2-yl-1-(2-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-3-naphthalen-1-yl-1-(1-phenyl-ethyl)-urea.

Especially preferred compounds are compounds of the general formula I wherein n is the integer 1 or 2, m is the integer 0, $R^5$ represents methyl, $R^6$ represents phenyl, $R^1$, $R^2$, $R^3$, $R^4$, and $R^7$ have the meaning given in the formula I above and X represents oxygen.

Examples of especially preferred compounds are:
3-Biphenyl-2-yl-(9-oxo-1,2,3,9-tetrahydro-pyrrolo[2,1-b]quinazolin-3-yl)-1-(1-phenyl-ethyl)-urea;
3-(2-Ethyl-phenyl)-1-(9-oxo-1,2,3,9-tetrahydro-pyrrolo[2,1-b]quinazolin-3-yl)-1-(1-phenyl-ethyl)-urea;
3-(2-Ethoxy-phenyl)-1-(9-oxo-1,2,3,9-tetrahydro-pyrrolo[2,1-b]quinazolin-3-yl)-1-(1-phenyl-ethyl)-urea;
3-Biphenyl-2-yl-1-(6-fluoro-9-oxo-1,2,3,9-tetrahydro-pyrrolo[2,1-b]quinazolin-3-yl)-1-(1-phenyl-ethyl)-urea;
1-(6-Fluoro-9-oxo-1,2,3,9-tetrahydro-pyrrolo[2,1-b]quinazolin-3-yl)-1-(1-phenyl-ethyl)-3-(2-n-propyl-phenyl)-urea;

1-(6-Fluoro-9-oxo-1,2,3,9-tetrahydro-pyrrolo[2,1-b]
quinazolin-3-yl)-1-(1-phenyl-ethyl)-3-(2-trifluo-
romethoxy-phenyl)-urea;
3-(2-Ethyl-phenyl)-1-(6-fluoro-9-oxo-1,2,3,9-tetrahydro-
pyrrolo[2,1-b]quinazolin-3-yl)-1-(1-phenyl-ethyl)-urea;
1-(7-Fluoro-9-oxo-1,2,3,9-tetrahydro-pyrrolo[2,1-b]
quinazolin-3-yl)-1-(phenyl-ethyl)-3-(2-n-propyl-phenyl)-
urea;
1-(6-Chloro-9-oxo-1,2,3,9-tetrahydro-pyrrolo[2,1-b]
quinazolin-3-yl)-1-(phenyl-ethyl)-3-(2-n-propyl-phenyl)-
urea;
1-(7-Chloro-9-oxo-1,2,3,9-tetrahydro-pyrrolo[2,1-b]
quinazolin-3-yl)-3-(2-isopropyl-phenyl)-1-(1-phenyl-
ethyl)-urea;
1-(7-Chloro-9-oxo-1,2,3,9-tetrahydro-pyrrolo[2,1-b]
quinazolin-3-yl)-1-(1-phenyl-ethyl)-3-(2-n-propyl-phe-
nyl)-urea;
1-(7-Chloro-9-oxo-1,2,3,9-tetrahydro-pyrrolo[2,1-b]
quinazolin-3-yl)-3-(2-ethyl-phenyl)-1-(1-phenyl-ethyl)-
urea;
1-(8-Chloro-9-oxo-1,2,3,9-tetrahydro-pyrrolo[2,1-b]
quinazolin-3-yl)-1-(1-phenyl-ethyl)-3-(2-n-propyl-phe-
nyl)-urea;
1-(8-Chloro-9-oxo-1,2,3,9-tetrahydro-pyrrolo[2,1-b]
quinazolin-3-yl)-3-(2-ethyl-phenyl)-1-(1-phenyl-ethyl)-
urea;
1-(8-Chloro-9-oxo-1,2,3,9-tetrahydro-pyrrolo[2,1-b]
quinazolin-3-yl)-1-(1-phenyl-ethyl)-3-(2-trifluo-
romethoxy-phenyl)-urea;
3-Biphenyl-2-yl-1-(8-chloro-9-oxo-1,2,3,9-tetrahydro-pyr-
rolo[2,1-b]quinazolin-3-yl)-1-(1-phenyl-ethyl)-urea;
1-(6,7-Difluoro-9-oxo-1,2,3,9-tetrahydro-pyrrolo[2,1-b]
quinazolin-3-yl)-1-(1-phenyl-ethyl)-3-(2-n-propyl-phe-
nyl)-urea;
1-(6,7-Difluoro-9-oxo-1,2,3,9-tetrahydro-pyrrolo[2,1-b]
quinazolin-3-yl)-3-(2-ethyl-phenyl)-1-(1-phenyl-ethyl)-
urea;
1-(11-oxo-6,8,9,11-tetrahydro-7H-pyrido[2,1-b]quinazolin-
6-yl)-1-(1-phenyl-ethyl)-3-(2-n-propyl-phenyl)-urea;
1-(3-Fluoro-11-oxo-6,8,9,11-tetrahydro-7H-pyrido[2,1-b]
quinazolin-6-yl)-1-(1-phenyl-ethyl)-3-(2-n-propyl-phe-
nyl)-urea;
3-(2-Ethyl-phenyl)-1-(3-fluoro-11-oxo-6,8,9,11-tetrahydro-
7H-pyrido[2,1-b]quinazolin-6-yl)-1-(1-phenyl-ethyl)-
urea;
1-(2,3-Difluoro-11-oxo-6,8,9,11-tetrahydro-7H-pyrido[2,1-
b]quinazolin-6-yl)-1-(1-phenyl-ethyl)-3-(2-n-propyl-phe-
nyl)-urea;
1-(2,3-Difluoro-11-oxo-6,8,9,11-tetrahydro-7H-pyrido[2,1-
b]quinazolin-6-yl)-3-(2-ethyl-phenyl)-1-(1-phenyl-
ethyl)-urea;
1-(2,3-Difluoro-11-oxo-6,8,9,11-tetrahydro-7H-pyrido[2,1-
b]quinazolin-6-yl)-3-(2-ethoxy-phenyl)-1-(1-phenyl-
ethyl)-urea;
1-(2-Fluoro-11-oxo-6,8,9,11-tetrahydro-7H-pyrido[2,1-b]
quinazolin-6-yl)-1-(1-phenyl-ethyl)-3-(2-n-propyl-phe-
nyl)-urea;
3-(2-Ethyl-phenyl)-1-(2-fluoro-11-oxo-6,8,9,11-tetrahydro-
7H-pyrido[2,1-b]quinazolin-6-yl)-1-(1-phenyl-ethyl)-
urea;
3-(2-Ethoxy-phenyl)-1-(2-fluoro-11-oxo-6,8,9,11-tetrahy-
dro-7H-pyrido[2,1-b]quinazolin-6-yl)-1-(1-phenyl-
ethyl)-urea;
1-(5-Fluoro-9-oxo-1,2,3,9-tetrahydro-pyrrolo[2,1-b]
quinazolin-3-yl)-1-((S)-1-phenyl-ethyl)-3-(2-n-propyl-
phenyl)-urea;
3-Biphenyl-2-yl-1-(5-Fluoro-9-oxo-1,2,3,9-tetrahydro-pyr-
rolo[2,1-b]quinazolin-3-yl)-1-((S)-1-phenyl-ethyl)-urea;
1-(5-Fluoro-9-oxo-1,2,3,9-tetrahydro-pyrrolo[2,1-b]
quinazolin-3-yl)-1-((S)-1-phenyl-ethyl)-3-(2-trifluo-
romethoxy-phenyl)-urea;
1-(9-Oxo-8-trifluoromethyl-1,2,3,9-tetrahydro-pyrrolo[2,1-
b]quinazolin-3-yl)-1-((S)-1-phenyl-ethyl)-3-(2-trifluo-
romethoxy-phenyl)-urea;
1-(9-Oxo-8-trifluoromethyl-1,2,3,9-tetrahydro-pyrrolo[2,1-
b]quinazolin-3-yl)-1-((S)-1-phenyl-ethyl)-3-(2-n-propyl-
phenyl)-urea;
3-(2-Ethyl-phenyl)-1-(9-oxo-8-trifluoromethyl-1,2,3,9-tet-
rahydro-pyrrolo[2,1-b]quinazolin-3-yl)-1-((S)-1-phenyl-
ethyl)-urea;
3-Biphenyl-1-(9-oxo-8-trifluoromethyl-1,2,3,9-tetrahydro-
pyrrolo[2,1-b]quinazolin-3-yl)-1-((S)-1-phenyl-ethyl)-
urea.

Examples of physiologically usable or pharmaceutically acceptable salts of the compounds of formula (I) are salts with physiologically compatible mineral acids such as hydrochloric acid, sulphuric or phosphoric acid; or with organic acids such as methanesulphonic acid, acetic acid, trifluoroacetic acid, citric acid, fumaric acid, maleic acid, tartaric acid, succinic acid or salicylic acid. The compounds of formula (I) with free acidic groups can also form salts with physiologically compatible bases. Examples of such salts are alkali metal, alkali earth metal, ammonium and alkylammonium salts such as Na, K, Ca or tetraalkylammonium salt. The compounds of formula (I) can also be present in the form of a zwitterion.

The compounds of formula (I) can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates and the meso-forms.

Preferred compounds as described above have $IC_{50}$ values below 500 nM; especially preferred compounds have $IC_{50}$ values below 100 nM which have been determinated with the FLIPR (Fluorometric Imaging Plates Reader) method described in the beginning of the experimental section.

The compounds of the general formula (I) and their pharmaceutically usable salts can be used for the treatment of diseases or disorders where an antagonist of a human orexin receptor is required such as obesity, diabetes, prolactinoma, cardiovascular disorders, cancer, pain, narcolepsy, sleep disorders like insomnia, sleep apnea, parasomnia, depression, anxiety, addictions, schizophrenia, neurodegenerative disorders and dementia.

The compounds of formula (I) and their pharmaceutically usable salts are particularly useful for the treatment of obesity and sleep disorders.

The compounds of formula I may also be used in combination with one or more other therapeutically useful substances e.g. with other orexin receptor antagonists, with lipid lowerer agents, with anorectic agents, with sleep inducing agents, with antidepressants or with other drugs beneficial for the prevention of treatment of obesity or sleep disorders.

The compounds of formula (I) and their pharmaceutically usable salts can be used as medicament (e.g. in the form of pharmaceutical preparations). The pharmaceutical preparations can be administered in enteral or oral form (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions).

The compounds of formula (I) and their pharmaceutically usable salts can be processed with pharmaceutically inert, inorganic or organic adjuvants for the production of tablets, coated tablets, dragées, and hard gelatine capsules. Lactose, corn starch or derivatives thereof, talc, stearic acid or its salts etc. can be used, for example, as such adjuvants for tablets, dragées, and hard gelatine capsules.

Suitable adjuvants for soft gelatine capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Morever, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The invention also relates to processes for the preparation of compounds of Formula I.

The compounds of general formula (I) of the present invention are prepared according to the general sequence of reactions outlined in the schemes below, wherein $R^1$, $R^2$, $R^3$, $R^4$, $R^5$, $R^6$, $R^7$ are as defined in formula (I) above. As the case may be any compound obtained with one or more optically active carbon atom may be resolved into pure enantiomers or diastereomers, mixtures of enantiomers or diastereomers, diastereomeric racemates and the meso-forms in a manner known per se.

The compounds obtained may also be converted into a pharmaceutically acceptable salt thereof in a manner known per se.

The compounds of general formula (I) may be prepared from the corresponding 2-amino benzoic acid derivatives with the desired lactam by treatment with $POCl_3$ (Karimov A. et al *Chemistry of Natural Compounds* 1982, 18, 4, 466–472; Bhardwaj V. et al *Indian Journal of Heterocyclic Chemistry* 1999, 8, 173–176). Subsequent radical bromination (Kamal A. et al *J. Org. Chem.* 2001, 66, 997–1001) followed by substitution with the corresponding primary amine gave the secondary amine intermediate which is then converted to the desired urea or thiourea compound by reaction with commercially available or synthetized isocyanate or isothiocyanate (Scheme 1) (March J. *Advanced Organic Chemistry-Reactions, Mechanisms and Structure* 1992, page 418, 4th edition, John Wiley & Sons)

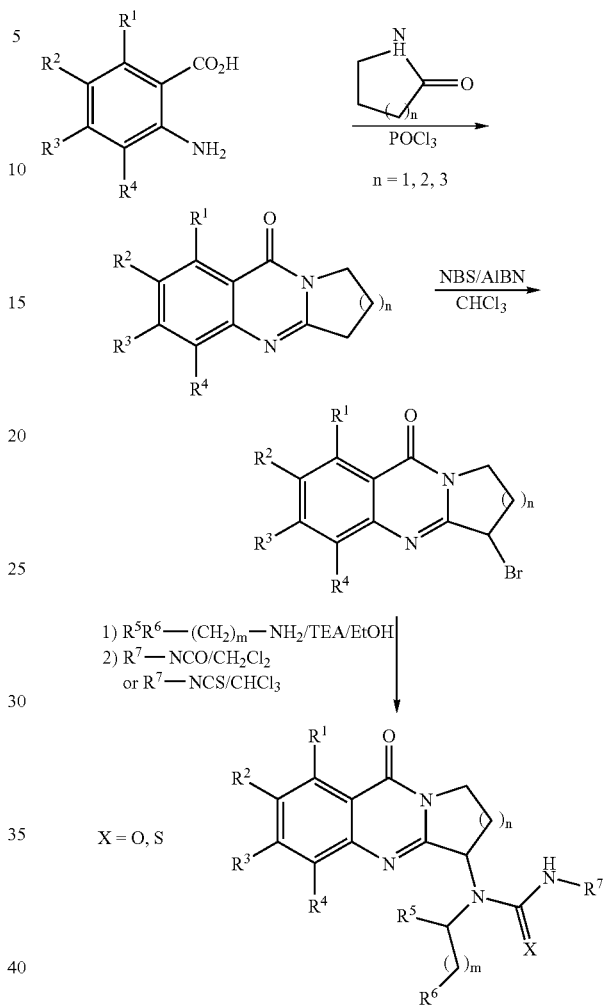

2-Amino benzoic acid derivatives wherein $R^1$ and $R^4$ are hydrogen and which are not commercially available might be prepared from benzoic acid derivatives using standard procedures (Giencke A. et al *Liebigs Ann. Chem.* 1990, 569–579; Follope M.-P. et al *Eur. J. med. Chem.* 1992, 27, 291–295) as described in Scheme 2.

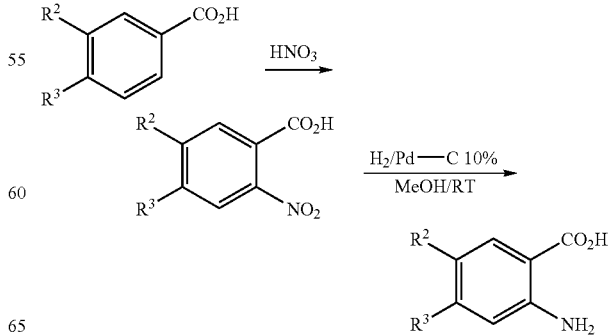

Furthermore, 2-amino benzoic acid derivatives may also be prepared from aniline derivatives by reaction with chloral hydrate in the presence of hydroxylamine hydrochloride followed by acidic treatment yielding the isatin intermediate. This was converted to the corresponding anthranilic acid derivative by reaction with hydrogen peroxide under basic conditions (Scheme 3) (Neal Bramson H. et al *J. Med. Chem.* 2001, 44, 4339–4358; Deady L. W. et al *J. Med. Chem.* 1997, 40, 2040–2046; Rowley M. et al *J. Med. Chem.* 1993, 36, 3386–3396; Hughes P. et al *J. Heterocyclic Chem.* 1990, 27, 2151–2163).

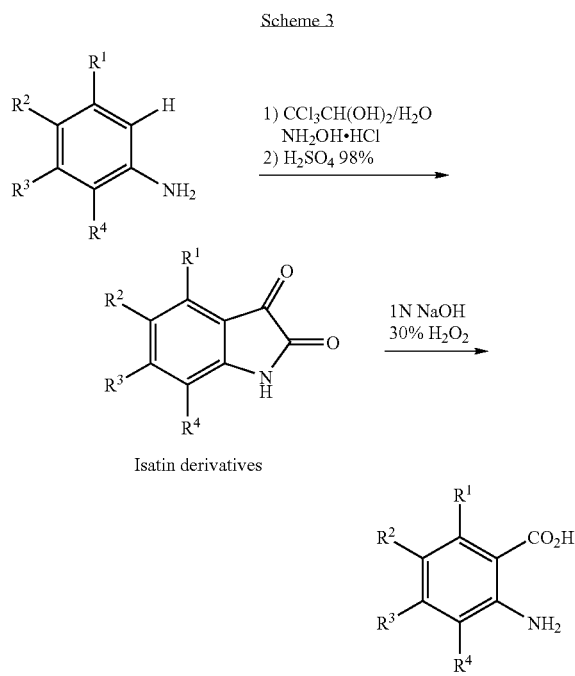

Isatin derivatives

EXPERIMENTAL SECTION

I. Biology

Determination of $OX_1$ and $OX_2$ Receptor Antagonistic Activities

The $OX_1$ and $OX_2$ receptor antagonistic activity of the compounds of formula (I) was determined in accordance with the following experimental method.

Experimental Method

Intracellular Calcium Measurements

Chinese hamster ovary (CHO) cells expressing the human orexin-1 receptor or the human orexin-2 receptor, were grown in culture medium (Ham F-12 with L-Glutamine) containing 300 µg/ml G418, 100 U/ml penicillin, 100 µg/ml streptomycin and 10% inactivated foetal calf serum (FCS).

The cells were seeded at 80'000 cells/well into 96-well black clear bottom sterile plates (Costar) which had been precoated with 1% gelatine in Hanks' Balanced Salt Solution (HBSS). All reagents were from Gibco BRL.

The seeded plates were incubated overnight at 37° C. in 5% $CO_2$.

Human orexin-A as an agonist was prepared as 1 mM stock solution in methanol:water (1:1), diluted in HBSS containing 0.1% bovine serum albumin (BSA) and 2 mM HEPES for use in the assay at a final concentration of 10 nM.

Antagonists were prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) was added to each well.

The 96-well plates were incubated for 60 min at 37° C. in 5% $CO_2$. The loading solution was then aspirated and cells were washed 3 times with 200 µl HBSS containing 2.5 mM probenecid, 0.1% BSA, 2 mM HEPES. 100 µl of that same buffer was left in each well. Within the Fluorescent Imaging Plate Reader (FLIPR, Molecular Devices), antagonists were added to the plate in a volume of 50 µl, incubated for 20 min and finally 100 µl of

TABLE 1

| | $IC_{50}$ (nM) | |
| --- | --- | --- |
| | $OX_1$ | $OX_2$ |
| Example 3 | 115 | 79 |
| Example 7 | 2400 | 27 |
| Example 28 | 153 | 17 |
| Example 30 | 261 | 16 |
| Example 33 | 127 | 18 |
| Example 40 | 37 | 14 |
| Example 41 | 52 | 14 |
| Example 44 | 67 | 27 |
| Example 49 | 12 | 16 |
| Example 50 | 14 | 18 |
| Example 51 | 28 | 21 | agonist was added. Fluorescence was measured for each well at 1 second intervals, and the height of each fluorescence peak was compared to the height of the fluorescence peak induced by 10 nM orexin-A with buffer in place of antagonist. For each antagonist, $IC_{50}$ value (the concentration of compound needed to inhibit 50% of the agonistic response) was determined. The $IC_{50}$ values of selected compounds are given in Table 1.

II. Chemistry

The following examples illustrate the preparation of pharmacologically active compounds of the invention but do not at all limit the scope thereof. All temperatures are stated in ° C.

All hydrochloride salts were prepared by dissolving the free-base in dichloromethane and treating with an excess of ethereal HCl (2M).

A. Abbreviations

| AIBN | 2,2'-azobisisobutyronitrile |
| --- | --- |
| BSA | Bovine serum albumine |
| CHO | Chinese hamster ovary |
| DMF | Dimethylformamide |
| eq | equivalent |
| ES | Electron spray |
| EtOH | Ethanol |
| FC | Flash chromatography |

-continued

| | |
|---|---|
| FCS | Foetal calf serum |
| FLIPR | Fluorescent imaging plate reader |
| HBSS | Hank's balanced salt solution |
| HEPES | 4-(2-Hydroxyethyl)-piperazine-1-ethanesulfonic acid |
| m | multiplet (NMR) |
| MeCN | Acetonitrile |
| MeOH | Methanol |
| MS | Mass spectroscopy |
| NBS | N-bromosuccinimide |
| NMR | Nuclear magnetic resonance |
| LC | Liquid chromatography |
| q | quartet (NMR) |
| $R_t$ | retention time |
| rt | Room temperature |
| s | singlet (NMR) |
| t | triplet (NMR) |
| TEA | Triethylamine |
| THF | Tetrahydrofuran |

B. 2,3-Dihydro-1H-pyrrolo[2,1-b]quinazolin-9-one derivatives

General Procedure

To a mixture of a 2-aminobenzoic acid derivative (1 g), 2-pyrrolidone (1.5 eq), was added carefully POCl$_3$ (2.5 mL). The resulting mixture was stirred at 100° C. for 1 h under nitrogen. After cooling, the reaction mixture was poured into ice-water, basified with sat. NaHCO$_3$, extracted with CH$_2$Cl$_2$ (3×100 mL). The combined extracts were dried (anhydrous MgSO$_4$), filtered and concentrated to give a crude brown-yellow viscous oil. FC (CH$_2$Cl$_2$/MeOH: 9/1) afforded the title compound as a solid.

1) 2,3-Dihydro-1H-pyrrolo[2,1-b]quinazolin-9-one

FC (CH$_2$Cl$_2$/MeOH: 9/1) afforded the title compound as a yellow solid (0.97 g, 71%).

LC-MS (MeCN/H$_2$O: 1/1): $R_t$=2.92 min. m/z=187 (M+1).

$^1$H-NMR (300 MHz; CDCl$_3$) δ 2.2 (2H, m), 3.2 (2H, m), 4.2 (2H, m), 7.4 (1H, t), 7.7 (1H, m), 8.3 (1H, d).

2) 5-Fluoro-2,3-dihydro-1H-pyrrolo[2,1-b]quinazolin-9-one

FC (CH$_2$Cl$_2$/MeOH: 9/1) afforded the title compound as brown solid (0.92 g, 70%).

LC-MS (MeCN/H$_2$O: 1/1): $R_t$=3.21 min. m/z=205 (M+1).

$^1$H-NMR (300 MHz; CDCl$_3$) δ 2.3 (2H, q), 3.25 (2H, t), 4.2 (2H, t), 7.4 (2H, m), 8.1 (1H, d).

3) 6-Fluoro-2,3-dihydro-1H-pyrrolo[2,1-b]quinazolin-9-one

FC (CH$_2$Cl$_2$/MeOH: 9/1) afforded the title compound as yellow crystals (0.79 g, 60%).

LC-MS (MeCN/H$_2$O: 1/1): $R_t$=3.16 min. m/z=206 (M+2).

$^1$H-NMR (300 MHz; CDCl$_3$) δ 2.3 (2H, q), 3.2 (2H, t), 4.2 (2H, t), 7.15 (1H, m), 7.4 (1H, dd), 8.3 (1H, t).

4) 7-Fluoro-2,3-dihydro-1H-pyrrolo[2,1-b]quinazolin-9-one

FC (CH$_2$Cl$_2$/MeOH: 9/1) afforded the title compound as yellow crystals (0.97 g, 74%).

LC-MS (MeCN/H$_2$O: 1/1): $R_t$=3.1 min. m/z=206 (M+2).

$^1$H-NMR (300 MHz; CDCl$_3$) δ 2.3 (2H, q), 3.2 (2H, t), 4.2 (2H, t), 7.4 (1H, m), 7.7 (1H, m), 7.95 (1H, dd).

5) 6,7-Difluoro-2,3-dihydro-1H-pyrrolo[2,1-b]quinazolin-9-one

FC (CH$_2$Cl$_2$/MeOH: 9/1) afforded the title compound as orange crystals (0.86 g, 67%).

LC-MS (MeCN/H$_2$O: 1/1): $R_t$=3.39 min. m/z=224 (M+2).

$^1$H-NMR (300 MHz; CDCl$_3$) δ 2.3 (2H, t), 3.2 (2H, t), 4.2 (2H, t), 7.4 (1H, m), 8.00 (1H, m).

6) 6-Chloro-2,3-dihydro-1H-pyrrolo[2,1-b]quinazolin-9-one

FC (CH$_2$Cl$_2$/MeOH: 9/1) afforded the title compound as yellow crystals (1.11 g, 86%).

LC-MS (MeCN/H$_2$O: 1/1): $R_t$=3.55 min. m/z=222 (M+2).

$^1$H-NMR (300 MHz; CDCl$_3$) δ 2.3 (2H, q), 3.2 (2H, t), 4.2 (2H, t), 7.4 (1H, d), 7.6 (1H, s), 8.2 (1H, d).

7) 7-Chloro-2,3-dihydro-1H-pyrrolo[2,1-b]quinazolin-9-one

FC (CH$_2$Cl$_2$/MeOH: 9/1) afforded the title compound as a yellow solid (1.14 g, 89%).

LC-MS (MeCN/H$_2$O: 1/1): $R_t$=3.52 min. m/z=222 (M+2).

$^1$H-NMR (300 MHz; CDCl$_3$) δ 2.3 (2H, q), 3.2 (2H, t), 4.2 (2H, t), 7.6 (2H, q), 8.3 (1H, s).

8) 8-Chloro-2,3-dihydro-1H-pyrrolo[2,1-b]quinazolin-9-one

FC (CH$_2$Cl$_2$/MeOH: 9/1) afforded the title compound as a yellow solid (0.97 g, 75%).

LC-MS (MeCN/H$_2$O: 1/1): $R_t$=3.30 min. m/z=222 (M+2).

$^1$H-NMR (300 MHz; CDCl$_3$) δ 2.3 (2H, q), 3.2 (2H, t), 4.2 (2H, t), 7.4 (1H, m), 7.6 (2H, m).

9) 8-Trifluoromethyl-2,3-dihydro-1H-pyrrolo[2,1-b]quinazolin-9-one

A mixture of 2-amino-6-trifluoromethyl-benzoic acid (0.97 g), 2-methoxypyrroline (0.703 g, 1.5 eq) in dry toluene (12 mL) was stirred at reflux for 3 h. The orange solution was then evaporated to dryness to give a crude orange solid FC (CH$_2$Cl$_2$/MeOH: 9/1) afforded the title compound as a yellow powder (0.89 g, 74%).

LC-MS (MeCN/H$_2$O: 1/1): $R_t$=3.90 min. m/z=255 (M+1).

$^1$H-NMR (300 MHz; CDCl$_3$) δ 2.3 (2H, q), 3.2 (2H, t), 4.25 (2H, t), 7.75 (1H, t), 7.85 (2H, d).

C. 3-Bromo-2,3-dihydro-1H-pyrrolo[2,1-b]quinazolin-9-one derivatives

General Procedure

A mixture of a 2,3-Dihydro-1H-pyrrolo[2,1-b]quinazolin-9-one derivative (1 eq), NBS (1 eq), AIBN (0.085 eq) in dry CHCl$_3$ (20 mL/ g) was stirred at reflux for 20 h under nitrogen. After cooling, the mixture was concentrated under reduced pressure, the resulting crude solid was purified by FC (AcOEt/heptane: 7/3) to give the title compound.

1) 3-Bromo-2,3-dihydro-1H-pyrrolo[2,1-b]quinazolin-9-one

FC (AcOEt/ heptane: 7/3) afforded the title compound as brown crystals (40%).

LC-MS (MeCN/H$_2$O:1/1): $R_t$=3.49 min. m/z=266 (M+1).

$^1$H-NMR (300 MHz; CDCl$_3$) δ 2.55–2.8 (2H, m), 4.1–4.5 (2H, m), 5.3 (1H, d), 7.5 (1H, m), 7.7 (1H, m), 8.3 (1H, d).

2) 3-Bromo-5-fluoro-2,3-dihydro-1H-pyrrolo[2,1-b]quinazolin-9-one

FC (AcOEt/heptane: 7/3) afforded the title compound as a n orange solid (35%).

LC-MS (MeCN/H$_2$O: 1/1): R$_t$=3.77 min. m/z=285 (M+2).

$^1$H-NMR (300 MHz; CDCl$_3$) δ 2.6–2.85 (2H, m), 4.2–4.45 (2H, m), 5.35 (1H, d), 7.5 (2H, m), 8.1 (1H, d).

3) 3-Bromo-6-fluoro-2,3-dihydro-1H-pyrrolo[2,1-b]quinazolin-9-one

FC (AcOEt/heptane: 7/3) afforded the title compound as a n orange solid (52%).

LC-MS (MeCN/H$_2$O: 1/1): R$_t$=3.70 min. m/z=284 (M+1).

$^1$H-NMR (300 MHz; CDCl$_3$) δ 2.55–2.8 (2H, m), 4.1–4.5 (2H, m), 5.3 (1H, d), 7.2 (1H, m), 7.5 (1H, m), 8.3 (1H, m).

4) 3-Bromo-7-fluoro-2,3-dihydro-1H-pyrrolo[2,1-b]quinazolin-9-one

FC (AcOEt/heptane: 7/3) afforded the title compound as a reddish solid (53%).

LC-MS (MeCN/H$_2$O: 1/1): R$_t$=3.65 min. m/z=284 (M+1).

$^1$H-NMR (300 MHz; CDCl$_3$) δ 2.6–2.85 (2H, m), 4.2–4.5 (2H, m), 5.3 (1H, d), 7.5 (1H, m), 7.7 (1H, m), 7.95 (1H, m).

5) 3-Bromo-6,7-difluoro-2,3-dihydro-1H-pyrrolo[2,1-b]quinazolin-9-one

FC (AcOEt/heptane: 7/3) afforded the title compound as a red solid (69%).

LC-MS (MeCN/H$_2$O: 1/1): R$_t$=4.01 min. m/z=302 (M+1).

$^1$H-NMR (300 MHz; CDCl$_3$) δ 2.55–2.8 (2H, m), 4.05–4.5 (2H, m), 5.3 (1H, d), 7.5 (1H, m), 8.1 (1H, m).

6) 3-Bromo-6-chloro-2,3-dihydro-1H-pyrrolo[2,1-b]quinazolin-9-one

FC (AcOEt/heptane: 7/3) afforded the title compound as a reddish solid (42%).

LC-MS (MeCN/H$_2$O: 1/1): R$_t$=4.16 min. m/z=300 (M+1).

$^1$H-NMR (300 MHz; CDCl$_3$) δ 2.6–2.85 (2H, m), 4.1–4.5 (2H, m), 5.3 (1H, d), 7.5 (1H, dd), 7.7 (1H, s), 8.3 (1H, d).

7) 3-Bromo-7-chloro-2,3-dihydro-1H-pyrrolo[2,1-b]quinazolin-9-one

FC (AcOEt/heptane: 7/3) afforded the title compound as a pink solid (49%).

LC-MS (MeCN/H$_2$O: 1/1): R$_t$=4.12 min. m/z=300 (M+1).

$^1$H-NMR (300 MHz; CDCl$_3$) δ 2.55–2.85 (2H, m), 4.1–4.5 (2H, m), 5.3 (1H, d), 7.7 (2H, s), 8.3 (1H, s).

8) 3-Bromo-8-chloro-2,3-dihydro-1H-pyrrolo[2,1-b]quinazolin-9-one

FC (AcOEt/heptane: 7/3) afforded the title compound as a violet powder (38%).

LC-MS (MeCN/H$_2$O: 1/1): R$_t$=3.56 min. m/z=300 (M+1).

$^1$H-NMR (300 MHz; CDCl$_3$) δ 2.55–2.85 (2H, m), 4.1–4.5 (2H, m), 5.3 (1H, d), 7.5 (1H, dd), 7.8 (2H, m).

9) 3-Bromo-8-trifluoromethyl-2,3-dihydro-1H-pyrrolo[2,1-b]quinazolin-9-one

FC (AcOEt/heptane: 7/3) afforded the title compound as a red solid (36%).

LC-MS (MeCN/H$_2$O: 1/1): R$_t$=4.47 min. m/z=334 (M+1).

$^1$H-NMR (300 MHz; CDCl$_3$) δ 2.55–2.85 (2H, m), 4.2–4.5 (2H, m), 5.3 (1H, d), 7.8 (1H, t), 7.9 (2H, m).

C. 3-(1-Phenyl-ethylamino)-2,3-dihydro-1H-pyrrolo[2,1-b]quinazolin-9-one derivatives

General Procedure

A mixture of a 3-bromo-2,3-dihydro-1H-pyrrolo[2,1-b]quinazolin-9-one derivative (0.56 g, 2.11 mmol), (D,L)-α-methylbenzylamine (1 eq), TEA (1.5 eq) in dry EtOH (10 mL), was stirred at reflux for 20 h under nitrogen. After cooling, the reaction mixture was combined with CH$_2$Cl$_2$/water and the aqueous phase was extracted twice with CH$_2$Cl$_2$. The combined extracts were dried (anhydrous MgSO$_4$), filtered and concentrated to give a dark green residue as mixture of diastereoisomers.

1) 3-(1-Phenyl-ethylamino)-2,3-dihydro-1H-pyrrolo[2,1-b]quinazolin-9-one

FC (AcOEt/heptane: 7/3) afforded the title compound as a dark green solid (69%).

LC-MS (MeCN/H$_2$O: 1/1): R$_t$=3.00 min. m/z=306 (M+1).

2) 6-Fluoro-3-(1-phenyl-ethylamino)-2,3-dihydro-1H-pyrrolo[2,1-b]quinazolin-9-one FC (AcOEt/heptane: 7/3) afforded the title compound as a dark oil (56%).

LC-MS (MeCN/H$_2$O: 1/1): R$_t$=3.18 min. m/z=324 (M+1).

3) 7-Fluoro-3-(1-phenyl-ethylamino)-2,3-dihydro-1H-pyrrolo[2,1-b]quinazolin-9-one FC (AcOEt/heptane: 7/3) afforded the title compound as a dark brown oil (62%).

LC-MS (MeCN/H$_2$O: 1/1): R$_t$=3.06 min. m/z=324 (M+1).

4) 6,7-Difluoro-3-(1-phenyl-ethylamino)-2,3-dihydro-1H-pyrrolo[2,1-b]quinazolin-9-one FC (AcOEt/heptane: 7/3) afforded the title compound as a dark green oil (42%).

LC-MS (MeCN/H$_2$O: 1/1): R$_t$=3.31 min. m/z=342 (M+1).

5) 6-Chloro-3-(1-phenyl-ethylamino)-2,3-dihydro-1H-pyrrolo[2,1-b]quinazolin-9-one FC (AcOEt/heptane: 7/3) afforded the title compound as a dark green oil (50%).

LC-MS (MeCN/H$_2$O: 1/1): R$_t$=3.40 min. m/z=340 (M+1).

6) 7-Chloro-3-(1-phenyl-ethylamino)-2,3-dihydro-1H-pyrrolo[2,1-b]quinazolin-9-one FC (AcOEt/heptane: 7/3) afforded the title compound as a dark brown oil (54%).

LC-MS (MeCN/H$_2$O: 1/1): R$_t$=3.34 min. m/z=340 (M+1).

7) 8-Chloro-3-(1-phenyl-ethylamino)-2,3-dihydro-1H-pyrrolo[2,1-b]quinazolin-9-one FC (AcOEt/heptane: 7/3) afforded the title compound as a dark brown oil (71%).

LC-MS (MeCN/H$_2$O: 1/1): R$_t$=3.21 min. m/z=340 (M+1).

8) 3-((S)-1-Phenyl-ethylamino)-8-trifluoromethyl-2,3-dihydro-1H-pyrrolo[2,1-b]quinazolin-9-one Reaction with the (S)-α-methylbenzylamine FC (AcOEt) afforded the title compound as a dark brown oil (68%).

LC-MS (MeCN/H$_2$O: 1/1): R$_t$=3.63 min. m/z=374 (M+1).

9) 5-Fluoro-3-((S)-1-phenyl-ethylamino)-2,3-dihydro-1H-pyrrolo[2,1-b]quinazolin-9-one Reaction with the (S)-α-methylbenzylamine FC (AcOEt) afforded the title compound as a dark green oil (58%).

LC-MS (MeCN/H$_2$O: 1/1): R$_t$=3.36 min. m/z=324 (M+1).

D. 6,7,8,9-Tetrahydro-pyrido[2,1-b]quinazolin-11-one derivatives

General Procedure

To a suspension of 2-aminobenzoic acid derivative (1 eq) in dry CHCl$_3$ (20 mL/g), was added slowly POCL$_3$ (1.3 eq) accompanied by stirring for 15 min at rt under nitrogen. Then δ-valerolactam (1.1 eq) was added portion wise over a period of 10 min, the reaction mixture was stirred at reflux under nitrogen for 3 h. Aqueous HCl 5% was added to the reaction mixture, the aqueous phase was separated (this operation was repeated three times). The combined aqueous extracts were clarified by adding active charcoal and filtered through celite. The resulting pale yellow solution was basified with concentrated aqueous ammonia and extracted with CH$_2$Cl$_2$ (three times). The combined organic extracts were washed with water, dried (anhydrous Na$_2$SO$_4$), concentrated under reduced pressure to give a solid which was used for the next step without further purification.

1) 6,7,8,9-Tetrahydro-pyrido[2,1-b]quinazolin-11-one

Light orange crystals (41%)

LC-MS (MeCN/H$_2$O: 1/1): R$_t$=2.83 min. m/z=201 (M+1).

$^1$H-NMR (300 MHz; CDCl$_3$) δ 2.00 (4H, m), 3.1 (2H, t), 4.1 (2H, t), 7.5 (1H, t), 7.6–7.8 (2H, m), 8.3 (1H, d).

2) 3-fluoro-6,7,8,9-tetrahydro-pyrido[2,1-b]quinazolin-11-one

Yellow crystals (44%)

LC-MS (MeCN/H$_2$O: 1/1): R$_t$=3.34 min. m/z=219 (M+1).

$^1$H-NMR (300 MHz; CDCl$_3$) δ 2.00 (4H, m), 3.0 (2H, t), 4.1 (2H, t), 7.1 (1H, m), 7.2 (1H, d), 8.3 (1H, t).

3) 2-fluoro-6,7,8,9-tetrahydro-pyrido[2,1-b]quinazolin-11-one

Yellow solid (56%)

LC-MS (MeCN/H$_2$O: 1/1): R$_t$=3.39 min. m/z=219 (M+1).

$^1$H-NMR (300 MHz; CDCl$_3$) δ 2.00 (4H, m), 3.0 (2H, t), 4.1 (2H, t), 7.4 (1H, m), 7.6 (1H, m), 7.9 (1H, dd).

4) 2,3-Difluoro-6,7,8,9-tetrahydro-pyrido[2,1-b]quinazolin-11-one

Yellow crystals (45%)

LC-MS (MeCN/H$_2$O: 1/1): R$_t$=3.82 min. m/z=237 (M+1).

$^1$H-NMR (300 MHz; CDCl$_3$) δ 2.00 (4H, m), 2.95 (2H, t), 4.1 (2H, t), 7.35 (1H, q), 8.0 (1H, t).

E. 6-Bromo-6,7,8,9-tetrahydro-pyrido[2,1-b]quinazolin-11-one derivatives

These compounds have been prepared as described for the 3-bromo-2,3-dihydro-1H-pyrrolo[2,1-b]quinazolin-9-one derivatives.

1) 6-Bromo-6,7,8,9-tetrahydro-pyrido[2,1-b]quinazolin-11-one

Pale yellow crystals (55%).

LC-MS (MeCN/H$_2$O: 1/1): R$_t$=3.86 min. m/z=280 (M+1).

$^1$H-NMR (300 MHz; CDCl$_3$) δ 2.1–2.6 (4H, m), 4.00 (1H, m), 4.4 (1H, m), 5.4 (1H, s), 7.5 (1H, t), 7.7 (2H, m), 8.3 (1H, d).

2) 6-Bromo-3-fluoro-6,7,8,9-Tetrahydro-pyrido[2,1-b]quinazolin-11-one

Pale yellow crystals (65%).

LC-MS (MeCN/H$_2$O: 1/1): R$_t$=4.21 min. m/z=298 (M+1).

$^1$H-NMR (300 MHz; CDCl$_3$) δ 2.1–2.6 (4H, m), 4.00 (1H, m), 4.4 (1H, m), 5.4 (1H, s), 7.2–7.5 (2H, m), 8.3 (1H, d).

3) 6-Bromo-2-fluoro-6,7,8,9-tetrahydro-pyrido[2,1-b]quinazolin-11-one

White solid (69%).

LC-MS (MeCN/H$_2$O: 1/1): R$_t$=4.20 min. m/z=298 (M+1).

$^1$H-NMR (300 MHz; CDCl$_3$) δ 2.1–2.6 (4H, m), 4.00 (1H, m), 4.4 (1H, m), 5.35 (1H, s), 7.5 (1H, m), 7.7 (1H, m), 7.9 (1H, dd).

4) 6-Bromo-2,3-difluoro-6,7,8,9-tetrahydro-pyrido[2,1-b]quinazolin-11-one

White solid (55%).

LC-MS (MeCN/H$_2$O: 1/1): R$_t$=4.49 min. m/z=316 (M+1).

$^1$H-NMR (300 MHz; CDCl$_3$) δ 2.1–2.6 (4H, m), 3.95 (1H, m), 4.4 (1H, m), 5.35 (1H, s), 7.45 (1H, t), 8.05 (1H, t).

F. 6-(1-Phenyl-ethylamino)-6,7,8,9-tetrahydro-pyrido[2,1-b]quinazolin-11-one derivatives These compounds have been prepared as decribed for the 3-(1-phenyl-ethylamino)-2,3-dihydro-1H-pyrrolo[2,1-b]quinazolin-9-one derivatives (mixture of diastereoisomers).

1) 6-(1-Phenyl-ethylamino)-6,7,8,9-tetrahydro-pyrido[2,1-b]quinazolin-11-one

Pale yellow solid (72%).

LC-MS (MeCN/H$_2$O: 1/1): R$_t$=2.98 and 3.19 min. m/z=320 (M+1).

2) 3-Fluoro-6-(1-phenyl-ethylamino)-6,7,8,9-tetrahydro-pyrido[2,1-b]quinazolin-11-one Yellow solid (40%).

LC-MS (MeCN/H$_2$O: 1/1): R$_t$=3.18 min. m/z=338 (M+1).

3) 2-Fluoro-6-(1-phenyl-ethylamino)-6,7,8,9-tetrahydro-pyrido[2,1-b]quinazolin-11-one Yellow solid (26%).

LC-MS (MeCN/H$_2$O: 1/1): R$_t$=3.14 min. m/z=338 (M+1).

4) 2,3-Difluoro-6-(1-phenyl-ethylamino)-6,7,8,9-tetrahydro-pyrido[2,1-b]quinazolin-11-one Yellow solid (40%).

LC-MS (MeCN/H$_2$O: 1/1): R$_t$=3.15 min. m/z=356 (M+1).

Example 1

1-(9-Oxo-1,2,3,9-tetrahydro-pyrrolo[2,1-b]quinazolin-3-yl)-1-(1-phenyl-ethyl)-3-(2-n-propyl-phenyl)-urea (mixture of diatereoisomers)

To a solution of 3-(1-phenyl-ethylamino)-2,3-dihydro-1H-pyrrolo[2,1-b]quinazolin-9-one (50 mg, 0.163 mmol) in dry $CH_2Cl_2$ (1 mL), was added 2-n-propylphenyl isocyanate (26.3 mg, 0.163 mmol). The resulting reaction mixture was stirred at rt under nitrogen for 20 h. The reaction mixture was then concentrated under reduced pressure and the residue was purified by FC (AcOEt/heptane: 7/3) to give the title compound as a white foam (45%). LC-MS (MeCN/$H_2O$: 1/1): $R_t$=3.00 min. m/z=467 (M+1).

Example 2

3-Biphenyl-2-yl-1-(9-oxo-1,2,3,9-tetrahydro-pyrrolo[2,1-b]quinazolin-3-yl)-1-(1-phenyl-ethyl)-urea (mixture of diatereoisomers)

In analogy to Example 1 using with 2-biphenyl isocyanate (1 eq).
FC (AcOEt/heptane: 7/3) afforded the title compound as a white foam (63%).
LC-MS (MeCN/$H_2O$: 1/1): $R_t$=4.89 and 5.49 min. m/z=500 (M).

Example 3

3-(2-Ethoxy-phenyl)-1-(9-oxo-1,2,3,9-tetrahydro-pyrrolo[2,1-b]quinazolin-3-yl)-1-(1-phenyl-ethyl)-urea (mixture of diatereoisomers)

In analogy to Example 1 using 2-ethoxyphenyl isocyanate (1 eq).
FC (AcOEt/heptane: 7/3) afforded the title compound as a white foam (55%).
LC-MS (MeCN/$H_2O$: 1/1): $R_t$=4.60 and 5.23 min. m/z=468 (M).

Example 4

3-(2-Ethyl-phenyl)-1-(6-fluoro-9-oxo-1,2,3,9-tetrahydro-pyrrolo[2,1-b]quinazolin-3-yl)-1-(1-phenyl-ethyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 2-ethylphenyl isocyanate (1 eq).
FC (AcOEt/heptane: 7/3) afforded the title compound as a white foam (62%).
LC-MS (MeCN/$H_2O$: 1/1): $R_t$=4.76 and 5.33 min. m/z=470 (M).

Example 5

3-Biphenyl-2-yl-1-(6-fluoro-9-oxo-1,2,3,9-tetrahydro-pyrrolo[2,1-b]quinazolin-3-yl)-1-(1-phenyl-ethyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 2-biphenylisocyanate (1 eq).
FC (AcOEt/heptane: 7/3) afforded the title compound as a white foam (82%).
LC-MS (MeCN/$H_2O$: 1/1): $R_t$=5.01 and 5.61 min. m/z=518 (M).

Example 6

1-(6-Fluoro-9-oxo-1,2,3,9-tetrahydro-pyrrolo[2,1-b]quinazolin-3-yl)-1-(1-phenyl-ethyl)-3-(2-n-propyl-phenyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 2-n-propylphenyl isocyanate (1 eq).
FC (AcOEt/heptane: 7/3) afforded the title compound as a beige powder (61%).
LC-MS (MeCN/$H_2O$: 1/1): $R_t$=5.06 and 5.61 min. m/z=484 (M).

Example 7

1-(6-Fluoro-9-oxo-1,2,3,9-tetrahydro-pyrrolo[2,1-b]quinazolin-3-yl)-1-(1-phenyl-ethyl)-3-(2-trifluoromethoxy-phenyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 2-trifluoromethoxyphenyl isocyanate (1 eq).
FC (AcOEt/heptane: 7/3) afforded the title compound as a white solid (72%).
LC-MS (MeCN/$H_2O$: 1/1): $R_t$=4.92 and 5.61 min. m/z=526 (M).

Example 8

1-(6-Fluoro-9-oxo-1,2,3,9-tetrahydro-pyrrolo[2,1-b]quinazolin-3-yl)-3-(2-isopropyl-phenyl)-1-(1-phenyl-ethyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 2-isopropylphenyl isocyanate (1 eq).
FC (AcOEt/heptane: 7/3) afforded the title compound as a white foam (70%).
LC-MS (MeCN/$H_2O$: 1/1): $R_t$=4.98 and 5.48 min. m/z=484 (M).

Example 9

1-(6-Fluoro-9-oxo-1,2,3,9-tetrahydro-pyrrolo[2,1-b]quinazolin-3-yl)-3-naphthalen-1-yl-1(1-phenyl-ethyl)-urea (mixture of diatereoisomers)

In analogy to Example 1 using 6-fluoro-3-(1-phenyl-ethylamino)-2,3-dihydro-1H-pyrrolo[2,1-b]quinazolin-9-one (1 eq) and 1-naphthyl isocyanate (1 eq).
FC (AcOEt/heptane: 7/3) afforded the title compound as a brown oil (77%).
LC-MS (MeCN/$H_2O$: 1/1): $R_t$=4.72 and 5.28 min. m/z=492 (M).

Example 10

1-(7-Fluoro-9-oxo-1,2,3,9-tetrahydro-pyrrolo[2,1-b]
quinazolin-3-yl)-1-(phenyl-ethyl)-3-(2-propyl-phenyl)-urea (mixture of diatereoisomers)

In analogy to Example 1 using 7-fluoro-3-(1-phenylethylamino)-2,3-dihydro-1H-pyrrolo[2,1-b]quinazolin-9-one (1 eq) and 2-n-propylphenyl isocyanate (1 eq).
FC (AcOEt/heptane: 7/3) afforded the title compound as an orange oil (75%).
LC-MS (MeCN/H$_2$O: 1/1): R$_t$=4.99 and 5.53 min. m/z=484 (M).

Example 11

1-(7-Fluoro-9-oxo-1,2,3,9-tetrahydro-pyrrolo[2,1-b]
quinazolin-3-yl)-1-(phenyl-ethyl)-3-(2-trifluoromethoxy-phenyl)-urea (mixture of diatereoisomers)

In analogy to Example 1 using 7-fluoro-3-(1-phenylethylamino)-2,3-dihydro-1H-pyrrolo[2,1-b]quinazolin-9-one (1 eq) and 2-trifluoromethoxyphenyl isocyanate (1 eq).
FC (AcOEt/heptane: 7/3) afforded the title compound as a brown oil (83%).
LC-MS (MeCN/H$_2$O: 1/1): R$_t$=4.85 and 5.52 min. m/z=526 (M+1).

Example 12

3-Biphenyl-2-yl-1-(7-fluoro-9-oxo-1,2,3,9-tetrahydro-pyrrolo[2,1-b]quinazolin-3-yl)-1(1-phenylethyl)-urea (mixture of diatereoisomers)

In analogy to Example 1 using 7-fluoro-3-(1-phenylethylamino)-2,3-dihydro-1H-pyrrolo[2,1-b]quinazolin-9-one (1 eq) and 2-biphenylisocyanate (1 eq).
FC (AcOEt/heptane: 7/3) afforded the title compound as a yellow brown oil (70%).
LC-MS (MeCN/H$_2$O: 1/1): R$_t$=5.02 and 5.59 min. m/z=518 (M).

Example 13

3-(2-Ethyl-phenyl)-1-(7-fluoro-9-oxo-1,2,3,9-tetrahydro-pyrrolo[2,1-b]quinazolin-3-yl)-1-(1-phenylethyl)-urea (mixture of diatereoisomers)

In analogy to Example 1 using 7-fluoro-3-(1-phenylethylamino)-2,3-dihydro-1H-pyrrolo[2,1-b]quinazolin-9-one (1 eq) and 2-ethylphenyl isocyanate (1 eq).
FC (AcOEt/heptane: 7/3) afforded the title compound as a beige foam (70%).
LC-MS (MeCN/H$_2$O: 1/1): R$_t$=4.77 and 5.32 min. m/z=470 (M).

Example 14

3-Biphenyl-2-yl-1-(6,7-difluoro-9-oxo-1,2,3,9-tetrahydro-pyrrolo[2,1-b]quinazolin-3-yl)-1-(1-phenylethyl)-urea (mixture of diatereoisomers)

In analogy to Example 1 using 6,7-difluoro-3-(1-phenylethylamino)-2,3-dihydro-1H-pyrrolo[2,1-b]quinazolin-9-one (1 eq) and 2-biphenylisocyanate (1 eq).
FC (AcOEt/heptane: 7/3) afforded the title compound as a pale grey foam (56%).
LC-MS (MeCN/H$_2$O: 1/1): R$_t$=5.27 and 5.84 min. m/z=536 (M).

Example 15

1-(6,7-Difluoro-9-oxo-1,2,3,9-tetrahydro-pyrrolo[2,
1-b]quinazolin-3-yl)-1-(phenyl-ethyl)-3-(2-trifluoromethoxy-phenyl)-urea (mixture of diatereoisomers)

In analogy to Example 1 using 6,7-difluoro-3-(1-phenylethylamino)-2,3-dihydro-1H-pyrrolo[2,1-b]quinazolin-9-one (1 eq) and 2-trifluromethoxyphenyl isocyanate (1 eq).
FC (AcOEt/heptane: 7/3) afforded the title compound as a brown foam (61%).
LC-MS (MeCN/H$_2$O: 1/1): R$_t$=5.07 and 5.74 min. m/z=544 (M).

Example 16

1-(6,7-Difluoro-9-oxo-1,2,3,9-tetrahydro-pyrrolo[2,
1-b]quinazolin-3-yl)-1-(1-phenyl-ethyl)-3-(2-n-propyl-phenyl)-urea (mixture of diatereoisomers)

In analogy to Example 1 using 6,7-difluoro-3-(1-phenylethylamino)-2,3-dihydro-1H-pyrrolo[2,1-b]quinazolin-9-one (1 eq) and 2-n-propylphenyl isocyanate (1 eq).
FC (AcOEt/heptane: 7/3) afforded the title compound as a brown foam (67%).
LC-MS (MeCN/H$_2$O: 1/1): R$_t$=5.22 and 5.74 min. m/z=502 (M).

Example 17

1-(7-Chloro-9-oxo-1,2,3,9-tetrahydro-pyrrolo[2,1-b]
quinazolin-3-yl)-3-(2-ethyl-phenyl)-1-(1-phenylethyl)-urea (mixture of diatereoisomers)

In analogy to Example 1 using 7-chloro-3-(1-phenylethylamino)-2,3-dihydro-1H-pyrrolo[2,1-b]quinazolin-9-one (1 eq) and 2-ethylphenyl isocyanate (1 eq).
FC (AcOEt/heptane: 7/3) afforded the title compound as a pale beige foam (66%).
LC-MS (MeCN/H$_2$O: 1/1): R$_t$=5.09 and 5.73 min. m/z=487 (M).

Example 18

1-(7-Chloro-9-oxo-1,2,3,9-tetrahydro-pyrrolo[2,1-b]
quinazolin-3-yl)-3-naphthalen-1-yl-1(1-phenylethyl)-urea (mixture of diatereoisomers)

In analogy to Example 1 using 7-chloro-3-(1-phenylethylamino)-2,3-dihydro-1H-pyrrolo[2,1-b]quinazolin-9-one (1 eq) and 1-naphthyl isocyanate (1 eq).
FC (AcOEt/heptane: 7/3) afforded the title compound as a beige solid (47%).
LC-MS (MeCN/H$_2$O: 1/1): R$_t$=4.99 and 5.61 min. m/z=509 (M).

Example 19

1-(7-Chloro-9-oxo-1,2,3,9-tetrahydro-pyrrolo[2,1-b]
quinazolin-3-yl)-3-(2-isopropyl-phenyl)-1-(1-phe-
nyl-ethyl)-urea (mixture of diatereoisomers)

In analogy to Example 1 using 7-chloro-3-(1-phenyl-
ethylamino)-2,3-dihydro-1H-pyrrolo[2,1-b]quinazolin-9-
one (1 eq) and 2-isopropylphenyl isocyanate (1 eq).
FC (AcOEt/heptane: 7/3) afforded the title compound as
a grey solid (87%).
LC-MS (MeCN/H$_2$O: 1/1): R$_t$ 5.30 and 5.81 min. m/z=501
(M).

Example 20

1-(7-Chloro-9-oxo-1,2,3,9-tetrahydro-pyrrolo[2,1-b]
quinazolin-3-yl)-1-(1-phenyl-ethyl)-3-(2-n-propyl-
phenyl)-urea (mixture of diatereoisomers)

In analogy to Example 1 using 7-chloro-3-(1-phenyl-
ethylamino)-2,3-dihydro-1H-pyrrolo[2,1-b]quinazolin-9-
one (1 eq) and 2-n-propylphenyl isocyanate (1 eq).
FC (AcOEt/heptane: 7/3) afforded the title compound as
a white foam (58%).
LC-MS (MeCN/H$_2$O: 1/1): R$_t$=5.34 and 5.92 min.
m/z=501(M).

Example 21

1-(7-Chloro-9-oxo-1,2,3,9-tetrahydro-pyrrolo[2,1-b]
quinazolin-3-yl)-1-(phenyl-ethyl)-3-(2-trifluo-
romethoxy-phenyl)-urea (mixture of diatereoiso-
mers)

In analogy to Example 1 using 7-chloro-3-(1-phenyl-
ethylamino)-2,3-dihydro-1H-pyrrolo[2,1-b]quinazolin-9-
one (1 eq) and 2-trifluoromethoxyphenyl isocyanate (1 eq).
FC (AcOEt/heptane: 7/3) afforded the title compound as
a pale brown foam (74%).
LC-MS (MeCN/H$_2$O: 1/1): R$_t$=5.18 and 5.92 min.
m/z=542 (M).

Example 22

3-Biphenyl-2-yl-1-(7-chloro-9-oxo-1,2,3,9-tetrahy-
dro-pyrrolo[2,1-b]quinazolin-3-yl)-1-(1-phenyl-
ethyl)-urea (mixture of diatereoisomers)

In analogy to Example 1 using 7-chloro-3-(1-phenyl-
ethylamino)-2,3-dihydro-1H-pyrrolo[2,1-b]quinazolin-9-
one (1 eq) and 2-biphenyl isocyanate (1 eq).
FC (AcOEt/heptane: 7/3) afforded the title compound as
a white foam (72%).
LC-MS (MeCN/H$_2$O: 1/1): R$_t$=5.36 and 5.99 min.
m/z=535 (M).

Example 23

3-Biphenyl-2-yl-1-(11-oxo-6,8,9,11-tetrahydro-7H-
pyrido[2,1-b]quinazolin-6-yl)-1-(1-phenyl-ethyl)-
urea (mixture of diatereoisomers)

In analogy to Example 1 using 6-(1-phenyl-ethylamino)-
6,7,8,9-tetrahydro-pyrido[2,1-b]quinazolin-11-one (1 eq)
and 2-biphenyl isocyanate (1 eq).
FC (AcOEt/heptane: 7/3) afforded the title compound as
a yellow oil (22%).
LC-MS (MeCN/H$_2$O: 1/1): R$_t$=4.99 and 5.80 min.
m/z=515 (M+1).

Example 24

1-(11-Oxo-6,8,9,11-tetrahydro-7H-pyrido[2,1-b]
quinazolin-6-yl)-1-(1-phenyl-ethyl)-3-(2-n-propyl-
phenyl)-urea (mixture of diatereoisomers)

In analogy to Example 1 using 6-(1-phenyl-ethylamino)-
6,7,8,9-tetrahydro-pyrido[2,1-b]quinazolin-11-one (1 eq)
and 2-n-propylphenyl isocyanate (1 eq).
FC (AcOEt/heptane: 7/3) afforded the title compound as
a beige foam (53%).
LC-MS (MeCN/H$_2$O: 1/1): R$_t$=5.18 and 5.86 min.
m/z=481 (M+1).

Example 25

3-(2-Ethyl-phenyl)-1-(11-oxo-6,8,9,11-tetrahydro-
7H-pyrido[2,1-b]quinazolin-6-yl)-1-(1-phenyl-
ethyl)-urea (mixture of diatereoisomers)

In analogy to Example 1 using 6-(1-phenyl-ethylamino)-
6,7,8,9-tetrahydro-pyrido[2,1-b]quinazolin-11-one (1 eq)
and 2-ethylphenyl isocyanate (1 eq).
FC (AcOEt/heptane: 7/3) afforded the title compound as
a yellow oil (72%).
LC-MS (MeCN/H$_2$O: 1/1): R$_t$=4.87 and 5.54 min.
m/z=467 (M+1).

Example 26

3-(2-Ethoxy-phenyl)-1-(11-oxo-6,8,9,11-tetrahydro-
7H-pyrido[2,1-b]quinazolin-6-yl)-1-(1-phenyl-
ethyl)-urea (mixture of diatereoisomers)

In analogy to Example 1 using 6-(1-phenyl-ethylamino)-
6,7,8,9-tetrahydro-pyrido[2,1-b]quinazolin-11-one (1 eq)
and 2-ethoxyphenyl isocyanate (1 eq).
FC (AcOEt/heptane: 7/3) afforded the title compound as
a beige solid (41%).
LC-MS (MeCN/H$_2$O: 1/1): R$_t$=4.81 and 5.67 min.
m/z=483 (M+1).

Example 27

3-Naphthalen-1-yl-1-(11-oxo-6,8,9,11-tetrahydro-
7H-pyrido[2,1-b]quinazolin-6-yl)-1-(1-phenyl-
ethyl)-urea (mixture of diatereoisomers)

In analogy to Example 1 using 6-(1-phenyl-ethylamino)-
6,7,8,9-tetrahydro-pyrido[2,1-b]quinazolin-11-one (1 eq)
and 1-naphthyl isocyanate (1 eq).
FC (AcOEt/heptane: 7/3) afforded the title compound as
a beige solid (28%).
LC-MS (MeCN/H$_2$O: 1/1): R$_t$=4.87 and 5.51 min.
m/z=489 (M+1).

Example 28

1-(2,3-Difluoro-11-oxo-6,8,9,11-tetrahydro-7H-pyrido[2,1-b]quinazolin-6-yl)-1-(1-phenyl-ethyl)-3-(2-n-propyl-phenyl)-urea (mixture of diatereoisomers)

In analogy to Example 1 using 2,3-difluoro-6-(1-phenyl-ethylamino)-6,7,8,9-tetrahydro-pyrido[2,1-b]quinazolin-11-one (1 eq) and 2-n-propylphenyl isocyanate (1 eq).

FC (AcOEt/heptane: 7/3) afforded the title compound as a beige foam (80%).

LC-MS (MeCN/H$_2$O: 1/1): R$_t$=6.13 min. m/z=517 (M+1).

Example 29

3-Biphenyl-2-yl-1-(2,3-difluoro-11-oxo-6,8,9,11-tetrahydro-7H-pyrido[2,1-b]quinazolin-6-yl)-1-(1-phenylethyl)-urea (mixture of diatereoisomers)

In analogy to Example 1 using 2,3-difluoro-6-(1-phenyl-ethylamino)-6,7,8,9-tetrahydro-pyrido[2,1-b]quinazolin-11-one (1 eq) and 2-biphenyl isocyanate (1 eq).

FC (AcOEt/heptane: 7/3) afforded the title compound as a beige foam (48%).

LC-MS (MeCN/H$_2$O: 1/1): R$_t$=5.57 and 6.22 min. m/z=551 (M+1).

Example 30

1-(2,3-Difluoro-11-oxo-6,8,9,11-tetrahydro-7H-pyrido[2,1-b]quinazolin-6-yl)-3-(2-ethyl-phenyl)-1-(1-phenyl-ethyl)-urea (mixture of diatereoisomers)

In analogy to Example 1 using 2,3-difluoro-6-(1-phenyl-ethylamino)-6,7,8,9-tetrahydro-pyrido[2,1-b]quinazolin-11-one (1 eq) and 2-ethylphenyl isocyanate (1 eq).

FC (AcOEt/heptane: 7/3) afforded the title compound as a beige foam (97%).

LC-MS (MeCN/H$_2$O: 1/1): R$_t$=5.35 and 5.92 min. m/z=503 (M+1).

Example 31

1-(2,3-Difluoro-11-oxo-6,8,9,11-tetrahydro-7H-pyrido[2,1-b]quinazolin-6-yl)-3-(2-ethoxy-phenyl)-1-(1-phenyl-ethyl)-urea (mixture of diatereoisomers)

In analogy to Example 1 using 2,3-difluoro-6-(1-phenyl-ethylamino)-6,7,8,9-tetrahydro-pyrido[2,1-b]quinazolin-11-one (1 eq) and 2-ethoxyphenyl isocyanate (1 eq).

FC (AcOEt/heptane: 7/3) afforded the title compound as a beige foam (60%).

LC-MS (MeCN/H$_2$O: 1/1): R$_t$=5.22 and 6.07 min. m/z=519 (M+1).

Example 32

3-Biphenyl-2-yl-1-(3-fluoro-11-oxo-6,8,9,11-tetrahydro-7H-pyrido[2,1-b]quinazolin-6-yl)-1-(1-phenyl-ethyl)-urea (mixture of diatereoisomers)

In analogy to Example 1 using 3-fluoro-6-(1-phenyl-ethylamino)-6,7,8,9-tetrahydro-pyrido[2,1-b]quinazolin-11-one (1 eq) and 2-biphenyl isocyanate (1 eq).

FC (AcOEt/heptane: 7/3) afforded the title compound as a beige foam (42%).

LC-MS (MeCN/H$_2$O: 1/1): R$_t$=5.38 and 6.10 min. m/z=533 (M+1).

Example 33

1-(3-Fluoro-11-oxo-6,8,9,11-tetrahydro-7H-pyrido[2,1-b]quinazolin-6-yl)-1-(1-phenyl-ethyl)-3-(2-n-propyl-phenyl)-urea (mixture of diatereoisomers)

In analogy to Example 1 using 3-fluoro-6-(1-phenyl-ethylamino)-6,7,8,9-tetrahydro-pyrido[2,1-b]quinazolin-11-one (1 eq) and 2-n-propylphenyl isocyanate (1 eq).

FC (AcOEt/heptane: 7/3) afforded the title compound as a beige foam (98%). LC-MS (MeCN/H$_2$O: 1/1): R$_t$=5.29 and 5.96 min. m/z=499 (M+1).

Example 34

3-(2-Ethoxy-phenyl)-1-(3-fluoro-11-oxo-6,8,9,11-tetrahydro-7H-pyrido[2,1-b]quinazolin-6-yl)-1-(1-phenylethyl)-urea (mixture of diatereoisomers)

In analogy to Example 1 using 3-fluoro-6-(1-phenyl-ethylamino)-6,7,8,9-tetrahydro-pyrido[2,1-b]quinazolin-11-one (1 eq) and 2-ethoxyphenyl isocyanate (1 eq).

FC (AcOEt/heptane: 7/3) afforded the title compound as a foam (88%).

LC-MS (MeCN/H$_2$O: 1/1): R$_t$=5.03 and 5.93 min. m/z=501 (M+1).

Example 35

3-(2-Ethyl-phenyl)-1-(3-fluoro-11-oxo-6,8,9,11-tetrahydro-7H-pyrido[2,1-b]quinazolin-6-yl)-1-(1-phenylethyl)-urea (mixture of diatereoisomers)

In analogy to Example 1 using 3-fluoro-6-(1-phenyl-ethylamino)-6,7,8,9-tetrahydro-pyrido[2,1-b]quinazolin-11-one (1 eq) and 2-ethylphenyl isocyanate (1 eq).

FC (AcOEt/heptane: 7/3) afforded the title compound as a foam (47%).

LC-MS (MeCN/H$_2$O: 1/1): R$_t$=5.07 and 5.74 min. m/z=485 (M+1).

Example 36

3-Biphenyl-2-yl-1-(2-fluoro-11-oxo-6,8,9,11-tetrahydro-7H-pyrido[2,1-b]quinazolin-6-yl)-1-(1-phenyl-ethyl)-urea (mixture of diatereoisomers)

In analogy to Example 1 using 2-fluoro-6-(1-phenyl-ethylamino)-6,7,8,9-tetrahydro-pyrido[2,1-b]quinazolin-11-one (1 eq) and 2-biphenyl isocyanate (1 eq).

FC (AcOEt/heptane: 7/3) afforded the title compound as a yellow powder (43%).

LC-MS (MeCN/H$_2$O: 1/1): R$_t$=5.38 and 6.07 min. m/z=533 (M+1).

Example 37

1-(2-Fluoro-11-oxo-6,8,9,11-tetrahydro-7H-pyrido[2,1-b]quinazolin-6-yl)-1-(1-phenyl-ethyl)-3-(2-n-propyl-phenyl)-urea (mixture of diatereoisomers)

In analogy to Example 1 using 2-fluoro-6-(1-phenyl-ethylamino)-6,7,8,9-tetrahydro-pyrido[2,1-b]quinazolin-1-one (1 eq) and 2-n-propylphenyl isocyanate (1 eq).

FC (AcOEt/heptane: 7/3) afforded the title compound as an orange-brown powder (53%).
LC-MS (MeCN/H$_2$O: 1/1): R$_t$=5.29 and 5.94 min. m/z=499 (M+1).

Example 38

3-(2-Ethoxy-phenyl)-1-(2-fluoro-11-oxo-6,8,9,11-tetrahydro-7H-pyrido[2,1-b]quinazolin-6-yl)-1-(1-phenylethyl)-urea (mixture of diatereoisomers)

In analogy to Example 1 using 2-fluoro-6-(1-phenyl-ethylamino)-6,7,8,9-tetrahydro-pyrido[2,1-b]quinazolin-11-one (1 eq) and 2-ethoxyphenyl isocyanate (1 eq).
FC (AcOEt/heptane: 7/3) afforded the title compound as a yellow powder (44%).
LC-MS (MeCN/H$_2$O: 1/1): R$_t$=5.03 and 5.86 min. m/z=501 (M+1).

Example 39

3-(2-Ethyl-phenyl)-1-(2-fluoro-11-oxo-6,8,9,11-tetrahydro-7H-pyrido[2,1-b]quinazolin-6-yl)-1-(1-phenylethyl)-urea (mixture of diatereoisomers)

In analogy to Example 1 using 2-fluoro-6-(1-phenyl-ethylamino)-6,7,8,9-tetrahydro-pyrido[2,1-b]quinazolin-11-one (1 eq) and 2-ethylphenyl isocyanate (1 eq).
FC (AcOEt/heptane: 7/3) afforded the title compound as a yellow powder (54%).
LC-MS (MeCN/H$_2$O: 1/1): R$_t$=5.07 and 5.72 min. m/z=485 (M+1).

Example 40

1-(8-Chloro-9-oxo-1,2,3,9-tetrahydro-pyrrolo[2,1-b]quinazolin-3-yl)-1-(phenyl-ethyl)-3-(2-trifluoromethoxy-phenyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 2-trifluoromethoxyphenyl isocyanate (1 eq).
FC (AcOEt/heptane: 7/3) afforded the title compound as a white foam (74%).
LC-MS (MeCN/H$_2$O: 1/1): R$_t$=4.97 and 5.74 min. m/z=542 (M).

Example 41

3-Biphenyl-2-yl-1-(8-chloro-9-oxo-1,2,3,9-tetrahydro-pyrrolo[2,1-b]quinazolin-3-yl)-1-(1-phenyl-ethyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 2-biphenylisocyanate (1 eq).
FC (AcOEt/heptane: 7/3) afforded the title compound as a yellow foam (70%).
LC-MS (MeCN/H$_2$O: 1/1): R$_t$=5.16 and 5.80 min. m/z=535 (M).

Example 42

1-(8-Chloro-9-oxo-1,2,3,9-tetrahydro-pyrrolo[2,1-b]quinazolin-3-yl)-3-(2-isopropyl-phenyl)-1-(1-phenyl-ethyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 2-isopropylphenyl isocyanate (1 eq).
FC (AcOEt/heptane: 7/3) afforded the title compound as a beige foam (70%).
LC-MS (MeCN/H$_2$O: 1/1): R$_t$=5.11 and 5.67 min. m/z=501 (M).

Example 43

1-(8-Chloro-9-oxo-1,2,3,9-tetrahydro-pyrrolo[2,1-b]quinazolin-3-yl)-3-naphthalen-1-yl-1(1-phenyl-ethyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 1-naphthyl isocyanate (1 eq).
FC (AcOEt/heptane: 7/3) afforded the title compound as a beige foam (57%).
LC-MS (MeCN/H$_2$O: 1/1): R$_t$=4.83 and 5.46 min. m/z=509 (M).

Example 44

1-(8-Chloro-9-oxo-1,2,3,9-tetrahydro-pyrrolo[2,1-b]quinazolin-3-yl)-1-(1-phenyl-ethyl)-3-(2-n-propyl-phenyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 2-n-propylphenyl isocyanate (1 eq).
FC (AcOEt/heptane: 7/3) afforded the title compound as a beige foam (64%).
LC-MS (MeCN/H$_2$O: 1/1): R$_t$=5.11 and 5.74 min. m/z=501 (M).

Example 45

1-(8-Chloro-9-oxo-1,2,3,9-tetrahydro-pyrrolo[2,1-b]quinazolin-3-yl)-3-(2-ethyl-phenyl)-1-(1-phenyl-ethyl)-urea (mixture of diatereoisomers)

In analogy to Example 1 using 8-chloro-3-(1-phenyl-ethylamino)-2,3-dihydro-1H-pyrrolo[2,1-b]quinazolin-9-one (1 eq) and 2-ethylphenyl isocyanate (1 eq).
FC (AcOEt/heptane: 7/3) afforded the title compound as a pale beige foam (83%).
LC-MS (MeCN/H$_2$O: 1/1): R$_t$=4.86 and 5.53 min. m/z=486 (M).

Example 46

1-(5-Fluoro-9-oxo-1,2,3,9-tetrahydro-pyrrolo[2,1-b]quinazolin-3-yl)-1-((S)-1-phenyl-ethyl)-3-(2-n-propyl-phenyl)-urea In analogy to Example 1 using 5-fluoro-3-((S)1-phenyl-ethylamino)-2,3-dihydro-1H-pyrrolo[2,1-b]quinazolin-9-one (1 eq) and 2-n-propylphenyl isocyanate (1 eq).
FC (AcOEt/heptane: 7/3) afforded the title compound as a pale beige foam (57%).

Example 47

3-Biphenyl-2-yl-1-(5-Fluoro-9-oxo-1,2,3,9-tetrahydro-pyrrolo[2,1-b]quinazolin-3-yl)-1-((S)-1-phenyl-ethyl)-urea In analogy to Example 1 using 5-fluoro-3-((S)1-phenyl-ethylamino)-2,3-dihydro-1H-pyrrolo[2,1-b]quinazolin-9-one (1 eq) and 2-biphenyl isocyanate (1 eq).

FC (AcOEt/heptane: 7/3) afforded the title compound as a green foam (73%).

LC-MS (MeCN/H$_2$O: 1/1): R$_t$=5.39 and 5.94 min. m/z=519 (M+1).

Example 48

1-(5-Fluoro-9-oxo-1,2,3,9-tetrahydro-pyrrolo[2,1-b]quinazolin-3-yl)-1-((S)-1-phenyl-ethyl)-3-(2-trifluoromethoxy-phenyl)-urea In analogy to Example 1 using 5-fluoro-3-((S)1-phenyl-ethylamino)-2,3-dihydro-1H-pyrrolo[2,1-b]quinazolin-9-one (1 eq) and 2-trifluoromethoxyphenyl isocyanate (1 eq).

FC (AcOEt/heptane: 7/3) afforded the title compound as a pale green solid (62%).

LC-MS (MeCN/H$_2$O: 1/1): R$_t$=5.13 and 5.72 min. m/z=527 (M+1).

Example 49

1-(9-Oxo-8-trifluoromethyl-1,2,3,9-tetrahydro-pyrrolo[2,1-b]quinazolin-3-yl)-1-((S)-1-phenyl-ethyl)-3-(2-trifluoromethoxy-phenyl)-urea In analogy to Example 1 using 3-((S)-1-Phenyl-ethylamino)-8-trifluoromethyl-2,3-dihydro-1H-pyrrolo[2,1-b]quinazolin-9-one (1 eq) and 2-trifluoromethoxyphenyl isocyanate (1 eq).

FC (AcOEt/heptane: 7/3) afforded the title compound as a beige foam (68%).

LC-MS (MeCN/H$_2$O: 1/1): R$_t$=5.39 and 6.14 min. m/z=577 (M+1).

Example 50

1-(9-Oxo-8-trifluoromethyl-1,2,3,9-tetrahydro-pyrrolo[2,1-b]quinazolin-3-yl)-1-((S)-1-phenyl-ethyl)-3-(2-n-propyl-phenyl)-urea In analogy to Example 1 using 3-((S)-1-Phenyl-ethylamino)-8-trifluoromethyl-2,3-dihydro-1H-pyrrolo[2,1-b]quinazolin-9-one (1 eq) and 2-n-propylphenyl isocyanate (1 eq).

FC (AcOEt/heptane: 7/3) afforded the title compound as a beige foam (54%).

LC-MS (MeCN/H$_2$O: 1/1): R$_t$=5.54 and 6.13 min. m/z=535 (M+1).

LC-MS (MeCN/H$_2$O: 1/1): R$_t$=5.27 and 5.74 min. m/z=485 (M+1).

Example 51

3-(2-Ethyl-phenyl)-1-(9-oxo-8-trifluoromethyl-1,2,3,9-tetrahydro-pyrrolo[2,1-b]quinazolin-3-yl)-1-((S)-1-phenyl-ethyl)-urea In analogy to Example 1 using 3-((S)-1-Phenyl-ethylamino)-8-trifluoromethyl-2,3-dihydro-1H-pyrrolo[2,1-b]quinazolin-9-one (1 eq) and 2-ethylphenyl isocyanate (1 eq).

FC (AcOEt/heptane: 7/3) afforded the title compound as a beige foam (62%).

LC-MS (MeCN/H$_2$O: 1/1): R$_t$=5.34 and 5.96 min. m/z=521 (M+1).

Example 52

3-Biphenyl-1-(9-oxo-8-trifluoromethyl-1,2,3,9-tetrahydro-pyrrolo[2,1-b]quinazolin-3-yl)-1-((S)-1-phenyl-ethyl)-urea In analogy to Example 1 using 3-((S)-1-Phenyl-ethylamino)-8-trifluoromethyl-2,3-dihydro-1H-pyrrolo[2,1-b]quinazolin-9-one (1 eq) and 2-biphenyl isocyanate (1 eq).

FC (AcOEt/heptane: 7/3) afforded the title compound as a beige foam (72%).

LC-MS (MeCN/H$_2$O: 1/1): R$_t$=5.64 and 6.22 min. m/z=569 (M+1).

The invention claimed is:

1. Compounds of the general formula (I)

formula (I)

wherein:
X is O or S;
n is the integer 1, 2, or 3;
m is the integer 0, 1, 2, 3;
$R^1$, $R^2$, $R^3$, $R^4$ independently represent cyano, nitro, halogen, hydrogen, hydroxy, lower alkyl, lower alkenyl, lower alkoxy, lower alkenyloxy, trifluoromethyl, trifluoromethoxy, cycloalkyloxy, aryloxy, aralkyloxy, heterocyclyloxy, heterocyclylalkyloxy, $R^8CO$—, $NR^9R^{10}CO$—, $R^9R^{10}N$—, $R^8OOC$—, $R^8SO_2NH$—, $R^{11}$—CO—NH—; or
$R^5$ represents aryl, aralkyl, lower alkyl, cycloalkyl, cycloalkyl-lower alkyl, heterocyclyl or heterocyclyl-lower alkyl;
$R^6$ represents hydrogen, lower alkyl, trifluoromethyl, —(CH$_2$)$_m$—OH, —(CH$_2$)$_m$—O-lower alkyl, —(CH$_2$)$_m$—CO$_2$H, —(CH$_2$)$_m$—CO$_2$-lower alkyl, —(CH$_2$)$_m$CONH$_2$, —(CH$_2$)$_m$—CONH-lower alkyl, or —(CH$_2$)$_m$—CON-(lower alkyl)$_2$, or —(CH$_2$)$_m$—N-(lower alkyl)$_2$;
$R^7$ represents aryl, aralkyl, lower alkyl, lower alkenyl, cycloalkyl, cycloalkyl-lower alkyl, heterocyclyl or heterocyclyl-lower alkyl;

R⁸ represents lower alkyl, aryl, aralkyl, heterocyclyl or heterocyclyl-lower alkyl; R⁹ and R¹⁰ independently represent hydrogen, alkyl, cycloalkyl, cycloalkyl-lower alkyl, aryl, aralkyl, heterocyclyl or heterocyclyl-lower alkyl;

R¹¹ represents lower alkyl, aryl, cycloalkyl, heterocyclyl, R⁹R¹⁰N— or R⁸O—; and optically pure enantiomers, mixtures of enantiomers, racemates, optically pure diastereoisomers, mixtures of diastereoisomers, diastereoisomeric racemates, mixture of diastereoisomeric racemates, or meso forms and pharmaceutically acceptable salts thereof.

2. Compounds of the general formula I according to claim 1, wherein n is integer 1 or 2, m is integer 0, 1 or 2, and X represents oxygen.

3. Compounds of the general formula I according to claim 1, wherein n is integer 1 or 2, m is integer 0, R⁵ represents methyl, R⁶ represents phenyl, and X represents oxygen.

4. A compound selected from the group consisting of 1-(9-Oxo-1,2,3,9-tetrahydro-pyrrolo[2,1-b]quinazolin-3-yl)-1-(1-phenyl-ethyl)-3-(2-n-propyl-phenyl)-urea;

3-Biphenyl-2-yl-(9-oxo-1,2,3,9-tetrahydro-pyrrolo[2,1-b]quinazolin-3-yl)-1-(1-phenyl-ethyl)-urea;

3-(2-Ethoxy-phenyl)-1-(9-oxo-1,2,3,9-tetrahydro-pyrrolo[2,1-b]quinazolin-3-yl)-1-(1-phenyl-ethyl)-urea;

3-(2-Ethyl-phenyl)-1-(6-fluoro-9-oxo-1,2,3,9-tetrahydro-pyrrolo[2,1-b]quinazolin-3-yl)-1-(1-phenyl-ethyl)-urea;

3-Naphthalen-1-yl-1-(9-oxo-1,2,3,9-tetrahydro-pyrrolo[2,1-b]quinazolin-3-yl)-1-(1-phenyl-ethyl)-urea;

3-(2-Ethyl-phenyl)-1-(6-fluoro-9-oxo-1,2,3,9-tetrahydro-pyrrolo[2,1-b]quinazolin-3-yl)-1-(1-phenyl-ethyl)-urea;

3-Biphenyl-2-yl-1-(6-fluoro-9-oxo-1,2,3,9-tetrahydro-pyrrolo[2,1-b]quinazolin-3-yl)-1-phenyl-ethyl)-urea;

1-(6-Fluoro-9-oxo-1,2,3,9-tetrahydro-pyrrolo[2,1-b]quinazolin-3-yl)-1-(1-phenyl-ethyl)-3-(2-propyl-phenyl)-urea;

1-(6-Fluoro-9-oxo-1,2,3,9-tetrahydro-pyrrolo[2,1-b]quinazolin-3-yl)-1-(1-phenyl-ethyl)-3-(2-trifluoromethoxy-phenyl)-urea;

1-(6-Fluoro-9-oxo-1,2,3,9-tetrahydro-pyrrolo[2,1-b]quinazolin-3-yl)-3-(2-isopropyl-phenyl)-1-(1-phenyl-ethyl)-urea;

1-(6-Fluoro-9-oxo-1,2,3,9-tetrahydro-pyrrolo[2,1-b]quinazolin-3-yl)-3-naphthalen-1-yl-1(1-phenyl-ethyl)-urea;

1-(7-Fluoro-9-oxo-1,2,3,9-tetrahydro-pyrrolo[2,1-b]quinazolin-3-yl)-1-(phenyl-ethyl)-3-(2-n-propyl-phenyl)-urea;

1-(7-Fluoro-9-oxo-1,2,3,9-tetrahydro-pyrrolo[2,1-b]quinazolin-3-yl)-1-(phenyl-ethyl)-3-(2-trifluoromethoxy-phenyl)-urea;

3-Biphenyl-2-yl-1-(7-fluoro-9-oxo-1,2,3,9-tetrahydro-pyrrolo[2,1-b]quinazolin-3-yl)-1-(1-phenyl-ethyl)-urea;

3-(2-Ethyl-phenyl)-1-(7-fluoro-9-oxo-1,2,3,9-tetrahydro-pyrrolo[2,1-b]quinazolin-3-yl)-1-(1-phenyl-ethyl)-urea;

1-(6-Chloro-9-oxo-1,2,3,9-tetrahydro-pyrrolo[2,1-b]quinazolin-3-yl)-1-(phenyl-ethyl)-3-(2-n-propyl-phenyl)-urea;

1-(7-Chloro-9-oxo-1,2,3,9-tetrahydro-pyrrolo[2,1-b]quinazolin-3-yl)-3-(2-ethyl-phenyl)-1-(1-phenyl-ethyl)-urea;

1-(7-Chloro-9-oxo-1,2,3,9-tetrahydro-pyrrolo[2,1-b]quinazolin-3-yl)-3-naphthalen-1-yl-1(1-phenyl-ethyl)-urea;

1-(7-Chloro-9-oxo-1,2,3,9-tetrahydro-pyrrolo[2,1-b]quinazolin-3-yl)-3-(2-isopropyl-phenyl)-1-(1-phenyl-ethyl)-urea;

1-(7-Chloro-9-oxo-1,2,3,9-tetrahydro-pyrrolo[2,1-b]quinazolin-3-yl)-1-(1-phenyl-ethyl)-3-(2-n-propyl-phenyl)-urea;

1-(7-Chloro-9-oxo-1,2,3,9-tetrahydro-pyrrolo[2,1-b]quinazolin-3-yl)-1-(phenyl-ethyl)-3-(2-trifluoromethoxy-phenyl)-urea;

3-Biphenyl-2-yl-1-(7-chloro-9-oxo-1,2,3,9-tetrahydro-pyrrolo[2,1-b]quinazolin-3-yl)-1-(1-phenyl-ethyl)-urea;

1-(8-Chloro-9-oxo-1,2,3,9-tetrahydro-pyrrolo[2,1-b]quinazolin-3-yl)-1-(1-(1-phenyl-ethyl)-3-(2-n-propyl-phenyl)-urea;

1-(8-Chloro-9-oxo-1,2,3,9-tetrahydro-pyrrolo[2,1-b]quinazolin-3-yl)-3-(2-ethyl-phenyl)-1-(1-phenyl-ethyl)-urea;

1-(8-Chloro-9-oxo-1,2,3,9-tetrahydro-pyrrolo[2,1-b]quinazolin-3-yl)-1-(1-phenyl-ethyl)-3-(2-trifluoromethoxy-phenyl)-urea;

3-Biphenyl-2-yl-1-(8-chloro-9-oxo-1,2,3,9-tetrahydro-pyrrolo[2,1-b]quinazolin-3-yl)-1-(1-phenyl-ethyl)-urea;

1-(8-Chloro-9-oxo-1,2,3,9-tetrahydro-pyrrolo[2,1-b]quinazolin-3-yl)-3-(2-isopropyl-phenyl)-1-(1-phenyl-ethyl)-urea;

1-(8-Chloro-9-oxo-1,2,3,9-tetrahydro-pyrrolo[2,1-b]quinazolin-3-yl)-3-naphthalen-1-yl-1-(1-phenyl-ethyl)-urea;

3-Biphenyl-2-yl-1-(6,7-difluoro-9-oxo-1,2,3,9-tetrahydro-pyrrolo[2,1-b]quinazolin-3-yl)-1-(1-phenyl-ethyl)-urea;

1-(6,7-Difluoro-9-oxo-1,2,3,9-tetrahydro-pyrrolo[2,1-b]quinazolin-3-yl)-1-(phenyl-ethyl)-3-(2-trifluoromethoxy-phenyl)-urea;

1-(6,7-Difluoro-9-oxo-1,2,3,9-tetrahydro-pyrrolo[2,1-b]quinazolin-3-yl)-1-(1-phenyl-ethyl)-3-(2-n-propyl-phenyl)-urea;

1-(6,7-Difluoro-9-oxo-1,2,3,9-tetrahydro-pyrrolo[2,1-b]quinazolin-3-yl)-3-(2-ethyl-phenyl)-1-(1-phenyl-ethyl)-urea;

3-Biphenyl-2-yl-1-butyl-1-(9-oxo-1,2,3,9-tetrahydro-pyrrolo[2,1-b]quinazolin-3-yl)-urea;

1-Butyl-1-(9-oxo-1,2,3,9-tetrahydro-pyrrolo[2,1-b]quinazolin-3-yl)-3-(2-n-propyl-phenyl)-urea;

1-Benzyl-3-biphenyl-2-yl-1-(9-oxo-1,2,3,9-tetrahydro-pyrrolo[2,1-b]quinazolin-3-yl)-urea;

1-Benzyl-3-(2-ethoxy-phenyl)-1-(9-oxo-1,2,3,9-tetrahydro-pyrrolo[2,1-b]quinazolin-3-yl)-urea;

1-Benzyl-1-(9-oxo-1,2,3,9-tetrahydro-pyrrolo[2,1-b]quinazolin-3-yl)-3-(2-n-propyl-phenyl)-urea;

3-Biphenyl-2-yl-1-(11-oxo-6,8,9,11-tetrahydro-7H-pyrido[2,1-b]quinazolin-6-yl)-1-(1-phenyl-ethyl)-urea;

1-(11-oxo-6,8,9,11-tetrahydro-7H-pyrido[2,1-b]quinazolin-6-yl)-1-(1-phenyl-ethyl)-3-(2-n-propyl-phenyl)-urea;

3-(2-Ethyl-phenyl)-1-(11-oxo-6,8,9,11-tetrahydro-7H-pyrido[2,1-b]quinazolin-6-yl)-1-(1-phenyl-ethyl)-urea;

3-(2-Ethoxy-phenyl)-1-(11-oxo-6,8,9,11-tetrahydro-7H-pyrido[2,1-b]quinazolin-6-yl)-1-(1-phenyl-ethyl)-urea;

3-Naphthalen-1-yl-1-(11-oxo-6,8,9,11-tetrahydro-7H-pyrido[2,1-b]quinazolin-6-yl)-1-(1-phenyl-ethyl)-urea;

3-Biphenyl-2-yl-1-(2,3-difluoro-11-oxo-6,8,9,11-tetrahydro-7H-pyrido[2,1-b]quinazolin-6-yl)-1-(1-phenyl-ethyl)-urea;
1-(2,3-Difluoro-11-oxo-6,8,9,11-tetrahydro-7H-pyrido[2,1-b]quinazolin-6-yl)-1-(1-phenyl-ethyl)-3-(2-n-propyl-phenyl)-urea;
1-(2,3-Difluoro-11-oxo-6,8,9,11-tetrahydro-7H-pyrido[2,1-b]quinazolin-6-yl)-3-(2-ethyl-phenyl)-1-(1-phenyl-ethyl)-urea;
1-(2,3-Difluoro-11-oxo-6,8,9,11-tetrahydro-7H-pyrido[2,1-b]quinazolin-6-yl)-3-(2-ethoxy-phenyl)-1-(1-phenyl-ethyl)-urea;
3-Biphenyl-2-yl-1-(3-fluoro-11-oxo-6,8,9,11-tetrahydro-7H-pyrido[2,1-b]quinazolin-6-yl)-1-(1-phenyl-ethyl)-urea;
1-(3-Fluoro-11-oxo-6,8,9,11-tetrahydro-7H-pyrido[2,1-b]quinazolin-6-yl)-1-(1-phenyl-ethyl)-3-(2-n-propyl-phenyl)-urea;
3-(2-Ethoxy-phenyl)-1-(3-fluoro-11-oxo-6,8,9,11-tetrahydro-7H-pyrido[2,1-b]quinazolin-6-yl)-1-(1-phenyl-ethyl)-urea;
3-(2-Ethyl-phenyl)-1-(3-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-1-(1-phenyl-ethyl)-3-(2-n-propyl-phenyl)-urea;
3-(2-Ethyl-phenyl)-1-(2-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-1-(1-phenyl-ethyl)-3-(2-trifluoromethoxy-phenyl)-urea;
3-(2-Ethoxy-phenyl)-1-(2-fluoro-11-oxo-6,8,9,11-tetrahydro-7H-pyrido[2,1-b]quinazolin-6-yl)-1-(1-phenyl-ethyl)-urea;
3-Biphenyl-2-yl-1-(2-fluoro-11-oxo-6,8,9,11-tetrahydro-7H-pyrido[2,1-b]quinazolin-6-yl)-1-(1-phenyl-ethyl)-urea;
1-(2-Fluoro-11-oxo-6,8,9,11-tetrahydro-7H-pyrido[2,1-b]quinazolin-6-yl)-3-naphthalen-1-yl-1-(1-phenyl-ethyl)-urea;
1-(5-Fluoro-9-oxo-1,2,3,9-tetrahydro-pyrrolo[2,1-b]quinazolin-3-yl)-1-((S)-1-phenyl-ethyl)-3-(2-n-propyl-phenyl)-urea;
3-Biphenyl-2-yl-1-(5-Fluoro-9-oxo-1,2,3,9-tetrahydro-pyrrolo[2,1-b]quinazolin-3-yl)-1((S)-1-phenyl-ethyl)-urea;
1-(5-Fluoro-9-oxo-1,2,3,9-tetrahydro-pyrrolo[2,1-b]quinazolin-3-yl)-1-((S)-1-phenyl-ethyl)-3-(2-trifluoromethoxy-phenyl)-urea;
1-(9-Oxo-8-trifluoromethyl-1,2,3,9-tetrahydro-pyrrolo[2,1-b]quinazolin-3-yl)-1-((S)-1-phenyl-ethyl)-3-(2-trifluoromethoxy-phenyl)-urea;
1-(9-Oxo-8-trifluoromethyl-1,2,3,9-tetrahydro-pyrrolo[2,1-b]quinazolin-3-yl)-1-((S)-1-phenyl-ethyl)-3-(2-n-propyl-phenyl)-urea;
3-(2-Ethyl-phenyl)-1-(9-oxo-8-trifluoromethyl-1,2,3,9-tetrahydro-pyrrolo[2,1-b]quinazolin-3-yl)-1-((S)-1-phenyl-ethyl)-urea; and
3-Biphenyl-1-(9-oxo-8-trifluoromethyl-1,2,3,9-tetrahydro-pyrrolo[2,1-b]quinazolin-3-yl)-1-((S)-1-phenyl-ethyl)-urea.

5. A pharmaceutical composition comprising one or more compounds of any one of claims 1 to 4, or a pharmaceutically acceptable salt thereof, and a pharmaceutically acceptable carrier and/or adjuvant.

6. A method of treating diseases or disorders, where an antagonist of a human orexin receptor is required, selected from the group consisting of pain, insomnia, and sleep apnea, comprising administering to a subject in need thereof an effective amount of a compound as claimed in any one of claims 1 to 4, or a pharmaceutically acceptable salt thereof.

7. A method of treating diabetes where an antagonist of a human orexin receptor is required, comprising administering to a subject in need thereof an effective amount of a compound as claimed in any one of claims 1 to 4, or a pharmaceutically acceptable salt thereof.

8. A method of treating diabetes where an antagonist of a human orexin receptor is required, comprising administering to a subject in need thereof an effective amount of a compound as claimed in any one of claims 1 to 4, or a pharmaceutically acceptable salt thereof.

* * * * *